United States Patent [19]
Kim et al.

[11] Patent Number: 5,889,013
[45] Date of Patent: *Mar. 30, 1999

[54] PYRIMIDINE ACYCLONUCLEOSIDE DERIVATIVES

[75] Inventors: Dae-Kee Kim, Seoul; Jongsik Gam, Kyungki-do; Ganghyeok Kim, Inchon; Young-Woo Kim, Seoul; Namkyu Lee, Kyungki-do; Jinsoo Lim, Seoul; Hun-Taek Kim, Seoul; Key Hyup Kim, Seoul, all of Rep. of Korea

[73] Assignee: Sunkyong Industries Co., Inc., Kyungki-do, Rep. of Korea

[*] Notice: This patent issued on a continued prosecution application filed under 37 CFR 1.53(d), and is subject to the twenty year patent term provisions of 35 U.S.C. 154(a)(2).

[21] Appl. No.: 545,682
[22] PCT Filed: Jul. 29, 1994
[86] PCT No.: PCT/KR94/00102
    § 371 Date: Jan. 4, 1996
    § 102(e) Date: Jan. 4, 1996
[87] PCT Pub. No.: WO95/23138
    PCT Pub. Date: Aug. 31, 1995

[30] Foreign Application Priority Data

Feb. 28, 1994 [KR] Rep. of Korea ................... 94-3794
Jul. 27, 1994 [KR] Rep. of Korea ................. 94-18324
Jul. 27, 1994 [KR] Rep. of Korea ................. 94-18325

[51] Int. Cl.$^6$ .................... A61K 31/505; C07D 239/02
[52] U.S. Cl. .................... 514/269; 514/279; 514/270; 514/274; 544/300; 544/301; 544/302; 544/303; 544/310; 544/311; 544/314
[58] Field of Search ............. 544/314, 300–303, 544/310, 311; 514/269, 279, 270, 274

[56] References Cited

U.S. PATENT DOCUMENTS

| | | | |
|---|---|---|---|
| 2,781,344 | 2/1957 | Comte et al. | 260/256.4 |
| 3,687,931 | 8/1972 | Verheyden et al. | 260/211.5 R |
| 3,755,295 | 8/1973 | Verheyden et al. | 260/211.5 R |
| 4,415,573 | 11/1983 | Ochi et al. | 424/251 |
| 4,613,604 | 9/1986 | Chu et al. | 514/274 |
| 4,868,187 | 9/1989 | Ogilivie | 514/269 |
| 5,077,280 | 12/1991 | Sommadossi et al. | 514/69 |
| 5,112,835 | 5/1992 | Miyasaka et al. | 544/302 |
| 5,141,943 | 8/1992 | Naguib et al. | 514/270 |
| 5,318,972 | 6/1994 | Miyasaka et al. | 514/269 |
| 5,461,060 | 10/1995 | Miyasaka et al. | 514/269 |
| 5,476,855 | 12/1995 | El Kouni et al. | 514/269 |

FOREIGN PATENT DOCUMENTS

| | | |
|---|---|---|
| 0 420 763 A2 | 4/1991 | European Pat. Off. . |
| 0 447 324 A1 | 9/1991 | European Pat. Off. . |
| 0 449 726 A1 | 10/1991 | European Pat. Off. . |
| WO89/09213 | 10/1989 | WIPO ............ C07D 239/55 |

OTHER PUBLICATIONS

H. Tanaka, et al., "Synthesis and Antiviral Activity of 1–[(2–Hydroxyethoxy)methyl–6–(phenylthio)thymine (HEPT) as Potent and Selective Anti–HIV–1 Agents" J. Med. Chem. 35, 4713–17 (1992).

H. Tanaka, et al., "Structure Activity Relationships of 1–[2–Hydroxyethoxy)methyl]–6–[(phenylthiothymine Analogues: Effect of Substitutions at the C–6 Phenyl Ring and at the C–5 Position on Anti–HIV–1 Activity" J. Med. Chem 35, 337–45 (1992).

Naganna M. Goudgaon and Raymond F. Schinazi, "Activity of Acyclic 6–(phenylselenenyl) pyrimidine Nucleosides aginast Human Immunodeficiency Viruses in Primary Lymphocytes", J. Med. Chem. vol. 34, 1991, pp. 3305–3309.

Bai–Chuan Pan, Zhi–Hao Chen, Giovanna Piras, Ginger E. Dutschman, Elizabeth C. Rowe, Yung–Chi Cheng and Shi-h–Hsi Chu, "Synthesis and Anti–HIV–1 Activities of 6–Arylthio and 6–Arylselenoacyclonucleosides", Journal of Heterocyclic Chemistry, vol. 31, No. 1, Jan.–Feb. 1994, pp. 177–185.

Goudgoan et al., J. Med. Chem. 1991, vol. 34, No. 11, pp. 3305–3309.

Goudgaon et al.., Antiviral Chem., Chemother., (1992), 3 (5), 263–6.

Tanaka et al., J. Med. Chem., (1991), 34, 349–357.

*Primary Examiner*—S. Mark Clardy
*Assistant Examiner*—Sabiha N. Qazi
*Attorney, Agent, or Firm*—Finnegan, Henderson, Farabow, Garrett & Dunner, L.L.P.

[57] ABSTRACT

The present invention relates to novel pyrimidine acyclonucleoside derivatives represented by the following general formula (I), antiviral agents containing the derivatives as the active ingredients and processes of preparation thereof.

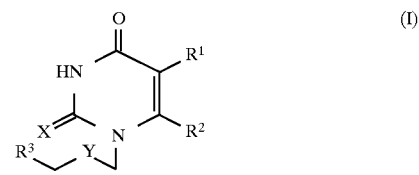

(I)

wherein $R^1$ is ethyl or isopropyl; $R^2$ is (3,5 dimethylphenyl)selenenyl; $R^3$ is phenyl or methyl; X is oxygen; and Y is oxygen.

9 Claims, No Drawings

PYRIMIDINE ACYCLONUCLEOSIDE DERIVATIVES

This application has been filed under 35 USC 371 as a national Stage application of PCT/KR94/00102 filed on Jul. 29, 1994.

FIELD OF THE INVENTION

The present invention relates to novel pyrimidine acyclonucleoside derivatives, antiviral agents containing the derivative as the active ingredients and processes of preparation therefor.

BACKGROUND OF THE INVENTION

AIDS (Acquired immunodeficiency syndrome), caused by human immunodeficiency virus (HIV), is one of the world's most serious health problems. 3'-Deoxy-3'-azidothymidine (AZT), which is available in the clinic, has been proven to improve the clinical and immunological status of patients with AIDS and AIDS-related complex. However, serious side effects such as anemia and leukopenia strongly limit its clinical usefulness. Although 2',3'-dideoxyinosine (DDI) and 2',3'-dideoxycytidine (DDC) have more recently been approved for the patients who do not tolerate AZT, they are also suffering from side effects such as peripheral neuropathy and pancreatitis. Therfore, there is an urgent need to develop a substance possessing higher antiviral activity and lower toxicity to the host cells. Various pyrimidine acyclonucleoside derivatives having (substituted) phenylthio group or (substituted) benzyl group at the 6-position of the pyrimidine ring have been disclosed and found to have effective antiviral activity against retrovirus (WO 89/09213, EP 420,763 A2, EP 449,726 A1). A few 6-phenylselenenyl substituted pyrimidine acyclonucleoside derivatives (*J. Med. Chem.* 1991, 34, 3305–3309, *Antiviral Chem. & Chemother.* 1992, 3(5), 263–266 and *J. Heterocyclic Chem.* 1194, 31, 177–185) have been synthesized, however, the antiviral activity against retrovirus is only marginal. The present inventors have synthesized a wide variety of novel pyrimidine acyclonucleoside derivatives having ethyl group or isopropyl group at the 5-position and having (substituted) phenylselenenyl group at the 6-position of the pyrimidine ring, and found that most of these pyrimidine acyclonucleoside derivatives possessed excellent antiretroviral activity to satisfy the above demand (KR Application No. 94-3794, 94-18324 and 94-18325). The present invention has been accomplishied based on this finding.

SUMMARY OF THE INVENTION

A primary objective of the present invention is to provide novel pyrimidine acyclonucleoside derivatives represented by the following general formula (I):

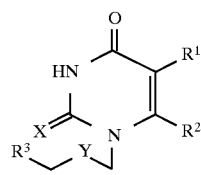

wherein $R^1$ represents ethyl group or isopropyl grop; $R^2$ represents phenylselenenyl group, optionally substituted with one or more suitable substituents selected from $C_1$–$C_3$ alkyl group or halogen atom; $R^3$ represents hydrogen atom, $C_1$–$C_3$ alkyl group, $C_1$–$C_3$ hydroxyalkyl group, acyloxyalkyl group, or phenyl group that is optionally substituted with one or more suitable substituents selected from $C_1$–$C_3$ alkyl group, $C_1$–$C_3$ alkoxy group or halogen atom; X represents oxygen atom or sulfur atom; and Y represents oxygen atom or methylene; with the proviso that $R^1$ does not represent ethyl group when $R^2$ represents phenylselenenyl group, $R^3$ represents methyl group or phenyl group, and X and Y represent oxygen atom.

Another objective of the present invention is to provide an antiviral agent containing pyrimidine acyclonucleoside derivative of general formula (I) or pharmaceutically acceptable salt thereof as active ingredient.

And another objective of the present invention is to provide processes of preparation for the pyrimidine acyclonucleoside derivative of general formula (I).

DETAILED DESCRIPTION OF THE INVENTION

The pyrimidine acyclonucleoside derivatives according to the invention are represented by the general formula (I). In the general formula(I), the group of $R^1$ represents ethyl group or isopropyl group. The group of $R^2$ represents phenylselenenyl group, and this group may be optionally substituted with one or more suitable substituents selected from $C_1$–$C_3$ alkyl group such as methyl, ethyl, propyl and isopropyl, or halogen atom such as fluorine, chlorine, bromine and iodine. The group of $R^3$ represents hydrogen atom; $C_1$–$C_3$ alkyl group such as methyl, ethyl and propyl; $C_1$–$C_3$ hydroxyalkyl group such as hydroxymethyl, hydroxyethyl and hydroxypropyl; acyloxyalkyl group such as acetyloxymethyl, acetyloxyethyl, acetyloxypropyl, propionyloxymethyl, propionyloxyethyl and propionyloxypropyl; or phenyl group that may be optionally substituted with one or more suitable substituents selected from $C_1$–$C_3$ alkyl group such as methyl, ethyl, propyl and isopropyl, $C_1$–$C_3$ alkoxy group such as methoxy, ethoxy, propoxy and isopropoxy, or halogen atom such as fluorine, chlorine, bromine and iodine. X represents oxygen atom or sulfur atom. Y represents oxygen atom or methylene.

Examples of the preferred compounds of the present invention are listed in Table 1 below.

TABLE 1

![Structure: pyrimidine core with HN-C(=O)-C(R¹)=C(R²)-N, X attached to C between HN and N, and N-CH2-Y-CH2-R³]

| Compound No. | R¹ | R² | R³ | X | Y |
|---|---|---|---|---|---|
| 1 | —C₂H₅ | —Se—C₆H₅ | —CH₂OH | S | O |
| 2 | —C₂H₅ | —Se—(3-CH₃-C₆H₄) | —CH₂OH | S | O |
| 3 | —C₂H₅ | —Se—(3,5-(CH₃)₂-C₆H₃) | —CH₂OH | S | O |
| 4 | —CH(CH₃)₂ | —Se—C₆H₅ | —CH₂OH | S | O |
| 5 | —CH(CH₃)₂ | —Se—(3-CH₃-C₆H₄) | —CH₂OH | S | O |
| 6 | —CH(CH₃)₂ | —Se—(3,5-(CH₃)₂-C₆H₃) | —CH₂OH | S | O |
| 7 | —C₂H₅ | —Se—C₆H₅ | —CH₂OH | O | O |
| 8 | —C₂H₅ | —Se—(3-CH₃-C₆H₄) | —CH₂OH | O | O |
| 9 | —C₂H₅ | —Se—(3,5-(CH₃)₂-C₆H₃) | —CH₂OH | O | O |

TABLE 1-continued

Structure: pyrimidinone with substituents R¹, R², R³, X, Y as shown.

| Compound No. | R¹ | R² | R³ | X | Y |
|---|---|---|---|---|---|
| 10 | —CH(CH$_3$)$_2$ | —Se—C$_6$H$_5$ (phenyl) | —CH$_2$OH | O | O |
| 11 | —CH(CH$_3$)$_2$ | —Se—(3-methylphenyl) | —CH$_2$OH | O | O |
| 12 | —CH(CH$_3$)$_2$ | —Se—(3,5-dimethylphenyl) | —CH$_2$OH | O | O |
| 13 | —C$_2$H$_5$ | —Se—(3,5-dimethylphenyl) | —CH$_2$OCCH$_3$ (with C=O) | O | O |
| 14 | —CH(CH$_3$)$_2$ | —Se—(3,5-dimethylphenyl) | —CH$_2$OCCH$_3$ (with C=O) | O | O |
| 15 | —C$_2$H$_5$ | —Se—C$_6$H$_5$ (phenyl) | —CH$_3$ | S | O |
| 16 | —C$_2$H$_5$ | —Se—(3-methylphenyl) | —CH$_3$ | S | O |
| 17 | —C$_2$H$_5$ | —Se—(3,5-dimethylphenyl) | —CH$_3$ | S | O |

TABLE 1-continued

Structure:
- Pyrimidinone core with HN-C(=O)-C(R¹)=C(R²)-N, where the ring nitrogen bears a CH₂-Y-CH₂-R³ group and X is the C=X at the 2-position.

| Compound No. | R¹ | R² | R³ | X | Y |
|---|---|---|---|---|---|
| 18 | —C₂H₅ | —Se—(2,5-difluorophenyl) | —CH₃ | S | O |
| 19 | —C₂H₅ | —Se—(phenyl) | phenyl | S | O |
| 20 | —C₂H₅ | —Se—(3-methylphenyl) | phenyl | S | O |
| 21 | —C₂H₅ | —Se—(3,5-dimethylphenyl) | phenyl | S | O |
| 22 | —CH(CH₃)₂ | —Se—(phenyl) | —CH₃ | S | O |
| 23 | —CH(CH₃)₂ | —Se—(3-methylphenyl) | —CH₃ | S | O |
| 24 | —CH(CH₃)₂ | —Se—(3,5-dimethylphenyl) | —CH₃ | S | O |
| 25 | —CH(CH₃)₂ | —Se—(2,5-difluorophenyl) | —CH₃ | S | O |
| 26 | —CH(CH₃)₂ | —Se—(phenyl) | phenyl | S | O |

TABLE 1-continued

[Structure: pyrimidine core with HN-C(=O)-C(R¹)=C(R²)-N, with X and R³-CH₂-Y-CH₂- substituents]

| Compound No. | R¹ | R² | R³ | X | Y |
|---|---|---|---|---|---|
| 27 | —CH(CH₃)₂ | 3-CH₃-phenyl-Se— | phenyl | S | O |
| 28 | —CH(CH₃)₂ | 3,5-(CH₃)₂-phenyl-Se— | phenyl | S | O |
| 29 | —C₂H₅ | 3-CH₃-phenyl-Se— | —CH₃ | O | O |
| 30 | —C₂H₅ | 3,5-(CH₃)₂-phenyl-Se— | —CH₃ | O | O |
| 31 | —C₂H₅ | 3-F-phenyl-Se— | —CH₃ | O | O |
| 32 | —C₂H₅ | 3,5-F₂-phenyl-Se— | —CH₃ | O | O |
| 33 | —C₂H₅ | 3,5-(CH₃)₂-phenyl-Se— | —H | O | O |
| 34 | —C₂H₅ | 3,5-(CH₃)₂-phenyl-Se— | —C₂H₅ | O | O |

TABLE 1-continued
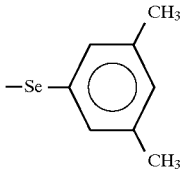
| Compound No. | R¹ | R² | R³ | X | Y |
|---|---|---|---|---|---|
| 35 | —C$_2$H$_5$ | 3,5-dimethylphenyl-Se— | —C$_3$H$_7$ | O | O |
| 37 | —C$_2$H$_5$ | 3,5-dimethylphenyl-Se— | phenyl | O | O |
| 38 | —C$_2$H$_5$ | 3,5-dimethylphenyl-Se— | phenyl | O | O |
| 39 | —C$_2$H$_5$ | 3,5-dimethylphenyl-Se— | 2-methylphenyl | O | O |
| 40 | —C$_2$H$_5$ | 3,5-dimethylphenyl-Se— | 3-methylphenyl | O | O |
| 41 | —C$_2$H$_5$ | 3,5-dimethylphenyl-Se— | 4-methylphenyl | O | O |
| 42 | —C$_2$H$_5$ | 3,5-dimethylphenyl-Se— | 2-methoxyphenyl | O | O |

TABLE 1-continued

Structure: pyrimidinone with R¹ at 5-position, R² at 6-position, N-CH₂-Y-CH₂-R³ at N1, X at 2-position.

| Compound No. | R¹ | R² | R³ | X | Y |
|---|---|---|---|---|---|
| 43 | —C₂H₅ | —Se—(2,5-dimethylphenyl) | 3-methoxyphenyl | O | O |
| 44 | —C₂H₅ | —Se—(2,5-dimethylphenyl) | 4-methoxyphenyl | O | O |
| 45 | —C₂H₅ | —Se—(2,5-dimethylphenyl) | 2-fluorophenyl | O | O |
| 46 | —C₂H₅ | —Se—(2,5-dimethylphenyl) | 3-fluorophenyl | O | O |
| 47 | —C₂H₅ | —Se—(2,5-dimethylphenyl) | 4-fluorophenyl | O | O |
| 48 | —CH(CH₃)₂ | —Se—(phenyl) | —CH₃ | O | O |
| 49 | —CH(CH₃)₂ | —Se—(3-methylphenyl) | —CH₃ | O | O |
| 50 | —CH(CH₃)₂ | —Se—(3,5-dimethylphenyl) | —CH₃ | O | O |

TABLE 1-continued
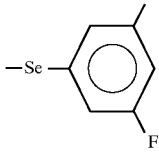
| Compound No. | R¹ | R² | R³ | X | Y |
|---|---|---|---|---|---|
| 51 | —CH(CH$_3$)$_2$ | 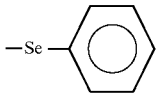 | —CH$_3$ | O | O |
| 52 | —CH(CH$_3$)$_2$ | 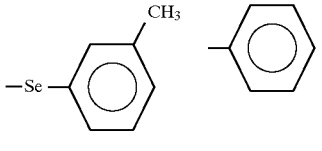 | 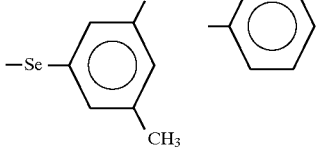 | O | O |
| 53 | —CH(CH$_3$)$_2$ | 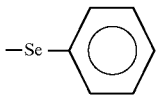 | 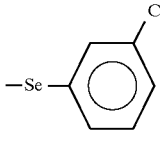 | O | O |
| 54 | —CH(CH$_3$)$_2$ | 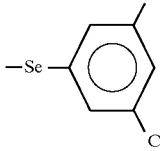 | 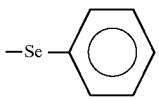 | O | O |
| 55 | —C$_2$H$_5$ | 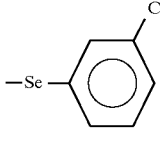 | —CH$_2$OH | S | CH$_2$ |
| 56 | —C$_2$H$_5$ |  | —CH$_2$OH | S | CH$_2$ |
| 57 | —C$_2$H$_5$ |  | —CH$_2$OH | S | CH$_2$ |
| 58 | —CH(CH$_3$)$_2$ |  | —CH$_2$OH | S | CH$_2$ |
| 59 | —CH(CH$_3$)$_2$ |  | —CH$_2$OH | S | CH$_2$ |

TABLE 1-continued
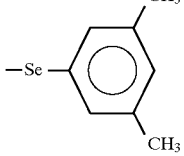
| Compound No. | R¹ | R² | R³ | X | Y |
|---|---|---|---|---|---|
| 60 | —CH(CH₃)₂ | —Se—⟨3,5-di-CH₃-C₆H₃⟩ | —CH₂OH | S | CH₂ |
| 61 | —CH(CH₃)₂ | —Se—C₆H₅ | —CH₃ | S | CH₂ |
| 62 | —CH(CH₃)₂ | —Se—⟨3-CH₃-C₆H₄⟩ | —CH₃ | S | CH₂ |
| 63 | —CH(CH₃)₂ | —Se—⟨3,5-di-CH₃-C₆H₃⟩ | —CH₃ | S | CH₂ |
| 64 | —C₂H₅ | —Se—C₆H₅ | —CH₃ | O | CH₂ |
| 65 | —C₂H₅ | —Se—⟨3,5-di-CH₃-C₆H₃⟩ | —CH₃ | O | CH₂ |
| 66 | —C₂H₅ | —Se—C₆H₅ | —CH₃ | S | CH₂ |
| 67 | —C₂H₅ | —Se—⟨3-CH₃-C₆H₄⟩ | —CH₃ | S | CH₂ |
| 68 | —C₂H₅ | —Se—⟨3,5-di-CH₃-C₆H₃⟩ | —CH₃ | S | CH₂ |

TABLE 1-continued $$\text{structure with HN-C(=O)-C(R^1)=C(R^2)-N, X connected, R^3-Y-CH_2 on N}$$

| Compound No. | $R^1$ | $R^2$ | $R^3$ | X | Y |
|---|---|---|---|---|---|
| 69 | $-C_2H_5$ | -Se-(3-F-phenyl) | $-CH_3$ | O | $CH_2$ |
| 70 | $-C_2H_5$ | -Se-(3,5-diCH$_3$-phenyl) | -H | O | $CH_2$ |
| 71 | $-C_2H_5$ | -Se-(3,5-diCH$_3$-phenyl) | $-C_2H_5$ | O | $CH_2$ |
| 72 | $-C_2H_5$ | -Se-(3,5-diCH$_3$-phenyl) | $-C_3H_7$ | O | $CH_2$ |
| 73 | $-C_2H_5$ | -Se-phenyl | phenyl | O | $CH_2$ |
| 74 | $-C_2H_5$ | -Se-(3,5-diCH$_3$-phenyl) | phenyl | O | $CH_2$ |
| 75 | $-C_2H_5$ | -Se-(3,5-diCH$_3$-phenyl) | 3-CH$_3$-phenyl | O | $CH_2$ |
| 76 | $-C_2H_5$ | -Se-(3,5-diCH$_3$-phenyl) | 4-CH$_3$-phenyl | O | $CH_2$ |

TABLE 1-continued

[Structure: pyrimidinone core with R¹ at C5, R² at C6, X=X at C2, N-CH₂-Y-CH₂-R³ at N1]

| Compound No. | R¹ | R² | R³ | X | Y |
|---|---|---|---|---|---|
| 77 | —C₂H₅ | —Se—[2,4-dimethylphenyl] | [2-methoxyphenyl] (H₃CO) | O | CH₂ |
| 78 | —C₂H₅ | —Se—[2,4-dimethylphenyl] | [4-methoxyphenyl] (OCH₃) | O | CH₂ |
| 79 | —C₂H₅ | —Se—[2,4-dimethylphenyl] | [3-fluorophenyl] | O | CH₂ |
| 80 | —C₂H₅ | —Se—[2,4-dimethylphenyl] | [4-fluorophenyl] | O | CH₂ |
| 81 | —CH(CH₃)₂ | —Se—[phenyl] | —CH₃ | O | CH₂ |
| 82 | —CH(CH₃)₂ | —Se—[2-methylphenyl] | —CH₃ | O | CH₂ |
| 83 | —CH(CH₃)₂ | —Se—[2,4-dimethylphenyl] | —CH₃ | O | CH₂ |
| 84 | —CH(CH₃)₂ | —Se—[phenyl] | [phenyl] | O | CH₂ |

TABLE 1-continued

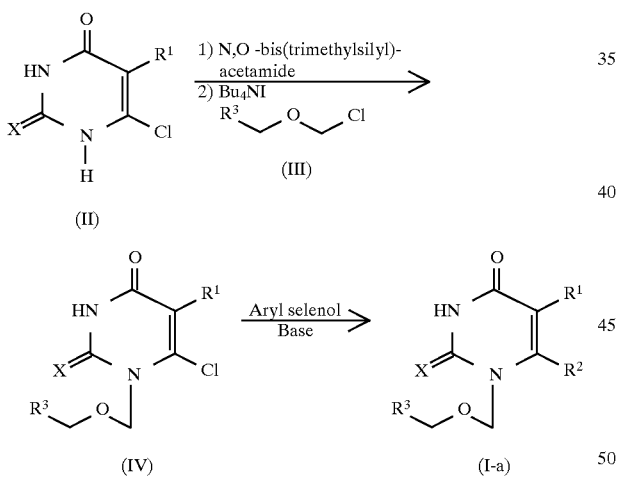

| Compound No. | R¹ | R² | R³ | X | Y |
|---|---|---|---|---|---|
| 85 | $-CH(CH_3)_2$ | -Se-C₆H₄-CH₃ (3-methylphenylselenyl) | phenyl | O | $CH_2$ |
| 86 | $-CH(CH_3)_2$ | -Se-C₆H₃(CH₃)₂ (3,5-dimethylphenylselenyl) | phenyl | O | $CH_2$ |

The compounds represented by the following general formula(I-a) may be prepared in accordance with the following reaction Scheme (1), (2) or (3):

Scheme (1)

(II) + (III) →[1) N,O-bis(trimethylsilyl)acetamide; 2) Bu₄NI] (IV) →[Aryl selenol / Base] (I-a)

wherein $R^1$, $R^2$, $R^3$ and X represent the same as defined in the general formula (I). As illustrated above, 1 mole of compound of the general formula (II) is treated with 2 to 4 moles of N,O-bis(trimethylsilyl)acetamide in dichloromethane at 0° to 50° C. for 0.5 to 5 hours. Then, about 0.01 to 0.05 moles of tetrabutylammonium iodide and 1 to 4 moles of chloromethyl ether represented by the general formula (III) are added to allow the reaction at a temperature of −50° to 50° C. for 0.5 to 5 hours to provide the compound represented by the general formula (IV). The compound of the general formula (IV) is reacted with 1 to 2 moles of aryl selenol and alcoholic solution (methanol or ethanol) of sodium hydroxide at 15° to 30° C. for 5 minutes to 5 hours to provide the compound represented by the general formula (I-a). The resulting compound of the present invention represented by the general formula (I-a) can be separated and purified by appropriate conventional methods such as column chromatography and recrystallization.

Scheme (2)

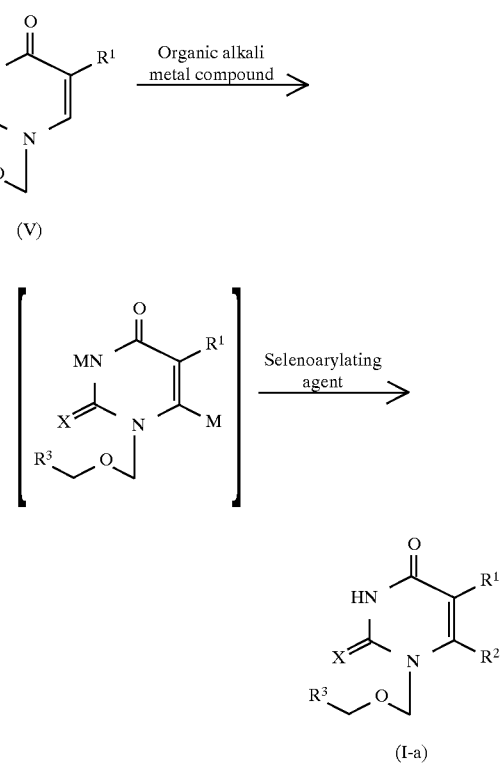

Scheme (3)

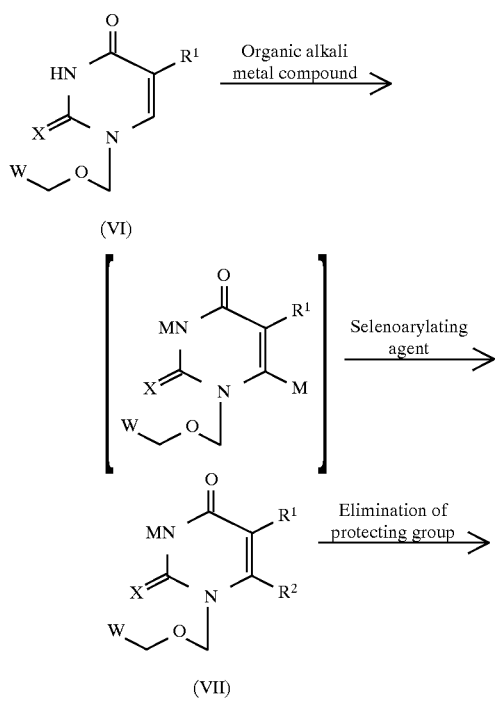

wherein $R^1$, $R^2$, $R^3$ and X represent the same as defined in the general formula(I), W represents the group of $R^3$ of which hydroxy group is protected, and M represents an alkali metal. Any conventional protective group which does not undergo elimination under alkaline condition may be used for the group of W, i.e., the pretection of the hydroxyl group of $R^3$. Examples of such a protective group are an aralkyl group such as benzyl, trityl, monomethoxytrityl, dimethoxytrityl, trimethoxytrityl, and the like; a silyl group such as trimethylsilyl, triethylsilyl, t-butyldimethylsilyl, t-butyldiphenylsilyl, and the like; and a substitued alkyl group such as tetrahydropyranyl, methoxymethyl, and the like. Among these protective groups, silyl groups may be most preferable. The compound of the general formula (V) or (VI) is firstly treated with an organic alkali metal compound in an ether solvent such as tetrahydrofuran and diethyl ether at a temperature of from −80° to 0° C. for 0.1 to 10 hours. Examples of the organic alkali metal compounds are lithium bis(trimethylsilyl)amide, potassium bis(trimethylsilyl)amide, sodium bis(trimethylsilyl)amide, lithium diisopropylamide (LDA) and lithium 2,2,6,6-tetramethylpiperidide (LTMP). Of these, lithium diisopropylamide (LDA) and lithium bis(trimethylsilyl)amide may be most preferable.

The organic alkali metal compound is generally used in an amount of 2 to 5 moles per mole of the compound represented by the general formula (V) or (VI). Then, about 1 to 5 moles of a selenoarylating agent is added to 1 mole of the compound represented by the general formula (V) or (VI) to allow the reaction at a temperature of from −80° to 30°C. for 0.1 to 24 hours to provide the compound represented by the general formula (I-a) or (VII). The selenoarylating agents should be those having a group of $R^2$ defined above. Examples of the selenoarylating agents are various diaryl diselenides. The compound represented by the general formula (V) or (VI) as a starting material can be prepared by a conventional method. Then, the protective group may be eliminated from the thus obtained compound represented by the general formula (VII). The elimination of the protective group can be carried out by a conventional method according to the kind of the protective group, for example, by hydrolysis, treatment with ammonium fluoride or catalytic reduction. The resulting compound of the present invention represented by the general formula (I-a) can be separated and purified by an apppropriate conventional method such as column chromatography and recrystallization.

The compounds of the invention where $R^3$ is a $C_1$–$C_3$ hydroxyalkyl group, which are obtained in reaction Scheme (3), may be converted into the corresponding compounds having a acyloxyalkyl group in accordance with the reaction Scheme (4) below:

Scheme (4)

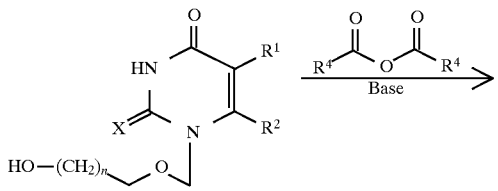

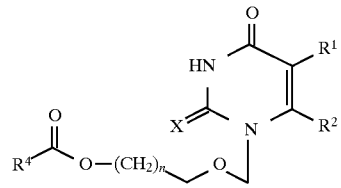

wherein $R^4$ represents alkyl, n represents an integer of 1 to 3, and the other symbols have the same meanings as defined hereinbefore. The reaction may be carried out in a suitable solvent such as dichloromethane, chloroform, pyridine, tetrahydrofuran and acetonitrile in the presence of a base in an amount of 1 to 10 moles of the starting compound at a suitable temperature from 0° C. to the boiling point of the solvent for 0.1 to 24 hours. Examples of the base include triethylamine, pyridine, imidazole, sodium carbonate, potassium carbonate and the like.

The compounds of the invention where X is a sulfur atom, which are obtained in the reaction Scheme (1), (2) or (3), may be converted to the corresponding compounds where X is an oxygen atom in accordance with the reaction Scheme (5) below:

Scheme (5)

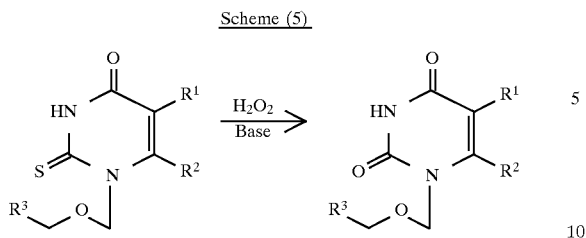

wherein $R^1$, $R^2$ and $R^3$ represent the same as defined in the general formula (I). The reaction may be carried out in an aqueous alkaline medium such as sodium hydroxide solution and potassium hydroxide solution by treating with 30–35% aqueous hydrogen peroxide solution in an amount of 1 to 20 times of the starting compound at a suitable temperature from 0° to 50° C. for 0.1 to 24 hours.

Besides the compounds represented by the following general formula(I-b) may be prepared in accordance with the following reaction Scheme (6):

formula (IX). The compound of general formula (IX) thus obtained is reacted with oxalyl chloride in benzene in the presence of a catalytic amount of N,N-dimethylformamide at 0° to 80° C. for 1 to 24 hours to give a acid chloride of general formula (X). The compound of general formula (X) is treated with silver cyanate or ammonium thiocyanate in benzene at reflux temperature for 0.5 to 5 hours followed by an appropriate amine at −78° to 40° C. for 0.5 to 5 hours to give an acryloylurea of general formula (XIa) or acryloylthiourea of general formula (XIb), respectively. The compound of general formula (XIa) is cyclized with 0.1 to 0.3 moles of methanesulfonic acid (MsOH)in acetic acid (AcOH) at 60 to 100 ° C for 1 to 24 hours to afford a 6-methylthiouracil of general formula (XII). Oxidation of the compound of general formula (XI) with m-chloroperbenzoic acid (MCPBA) in benzene at reflux temperature for 1 to 24 hours gave a 6-methylsulfonyluracil of general formula (XIII). The compound of general formula (XIb) is cyclized with 1 to 3 moles of methanesulfonic acid in acetic acid at 15° to 30° C. for 5 minutes to 5 hours to afford a compound of general formula (XIV). The compound of general

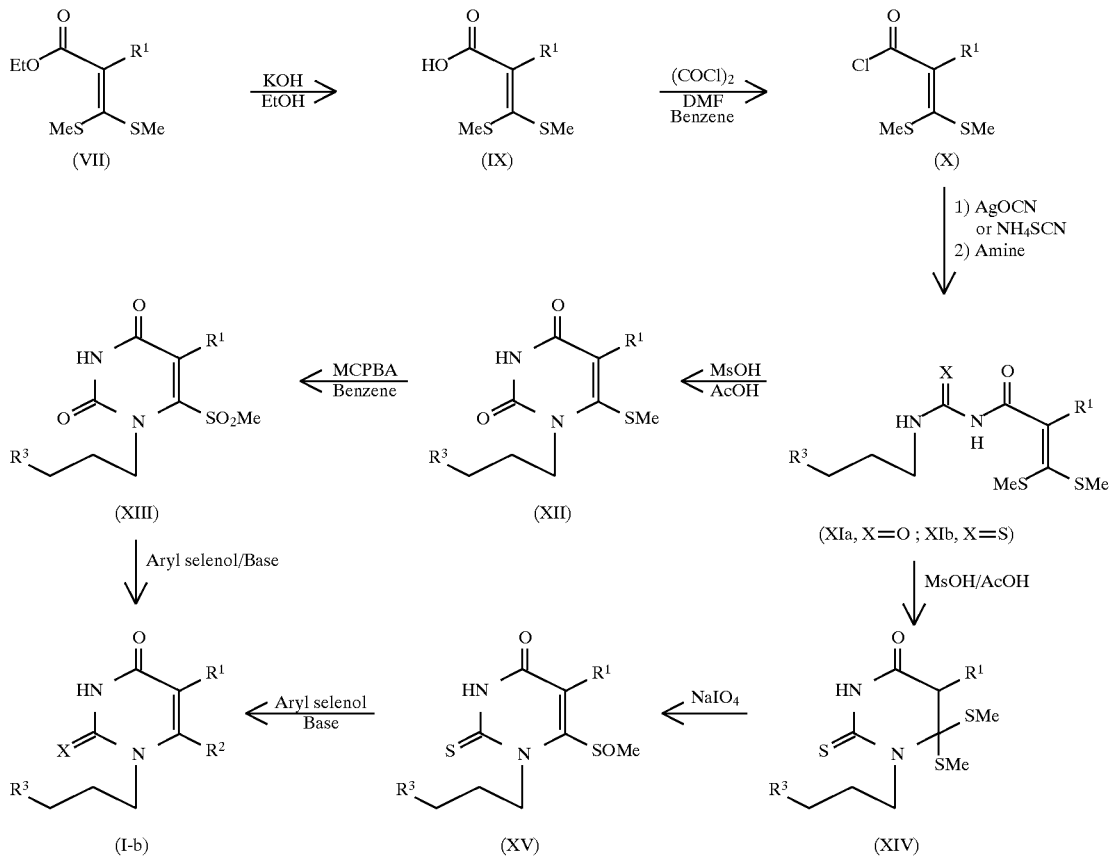

Scheme (6)

wherein $R^1$, $R^2$, $R^3$ and X represent the same as defined in the general formula (I). As illustrated above, first, a readily prepared compound of general formula (VIII) in accordance with the method described in *J. Chem. Soc., Chem. Commun.*, 684 (1989) or *Bull. Inst. Chem. Res., Kyoto Univ.*, 68, 199 (1990), is treated with aqueous potassium hydroxide solution in ethanol at reflux temperature for 3 to 72 hours to obtain a acid of general formula (XIV) is treated with 3 to 10 moles of aqueous solution of sodium periodate in methanol at reflux temperature for 1 to 5 hours to give a 6-methylsulfinyl-2-thiouracil of general formula (XV). Finally, the compound of general formula (XIII) or general formula (XV) is reacted with 1 to 2 moles of aryl selenol and methanolic solution of sodium hydroxide at 15° to 30° C. for 5 minutes to 5 hours to provide the compound represented by the general formula (I-b). The aryl selenol should be those having a group of $R^2$ defined above. The resulting compound of the present invention represented by the general formula (I-b) can be separated and purified by an appropriate conventional method such as column chromatography and recrystallization.

The pyrimidine acyclonucleoside derivative of the present invention may be made into a pharmaceutically acceptable salt by conventional methods. Examples of such salts may include alkali metal salts such as sodium salt, potassium salt and the like; alkaline earth metal salts such as magnesium salt and the like; and ammonium salts such as ammonium salt, methylammonium salt, dimethylammonium salt, trimethylammonium salt, tetramethylammonium salt and the like.

The pyrimidine acyclonucleoside derivatives of the present invention can be administered to a patient through any of the usual routes such as oral, parenteral and local administrations for the purpose of preventing infection of retroviruses and the like or treating infectious diseases caused by these viruses. The effective dose of the pyrimidine acyclonucleoside derivative may vary with the age, physical condition, body weight and the like of each patient. In general, the appropriate administration dose of the derivative of the present invention may be in the range of from 1 to 100 mg/kg (body weight)/day, preferably 5 to 50 mg/kg (body weight)/day. Administration of the derivative of the present invention may be made once a day or a few times a day within the above range of dose. The compounds of the present invention are generally prepared in a pharmaceutical composition with suitable carrier, excipient and other additives. The carriers may be in either a solid or a liquid form. Examples of solid carriers may include lactose, kaolin, sucrose, crystalline cellulose, corn starch, talc, pectin, agar, stearic acid, magnesium stearate, lecithin, sodium chloride and the like. Examples of liquid carriers may include glycerin, peanut oil, polyvinyl pyrrolidone, olive oil, ethanol, benzyl alcohol, propylene glycol, water and the like. The antiviral agent of the present invention can be made into various forms.

For example, when solid carriers are used, the antiviral agent can be made into tablet, capsule, powder, granule, suppository, troche and the like. When liquid carriers are used, it can be made into emulsion, syrup, soft gelatin capsule, gel, paste, injection solution and the like. The novel pyrimidine acyclonucleoside derivatives according to the present invention have an effective antiviral activity against viruses such as retrovirus and have a relatively low toxicity againt the host cell, therfore, the derivatives of the present invention are extremely useful as an active ingredient of antiviral agent.

EXAMPLE

The present invention is further illustrated in the following example, which should not be taken to limit the scope of the invention.

Preparative Example 1

Preparation of 6-chloro-1-(ethoxymethyl)-5-isopropyluracil (a compound of the general formula (IV) wherein $R^1=CH(CH_3)_2$, $R^3=CH_3$ and $X=O$)

To a stirred suspension of 6-chloro-5-isopropyluracil (566 mg, 3.0 mmol) in anhydrous $CH_2Cl_2$ (9 mL) at room temperature under a nitrogen atmosphere was slowly added N,O-bis(trimethylsilyl)acetamide (1.41 g, 6.6 mmol, 1.72 mL) via a syringe and the mixture was stirred for an additional 2 h at room temperature. To the resulting clear reaction mixture was added $Bu_4NI$ (11 mg, 0.03 mmol) in one portion at room temperature and the mixture was cooled to 0° C. immediately. Chloromethyl ethyl ether (591 mg, 6.0 mmol, 0.58 mL) was slowly added to the reaction mixture at 0° C. and the mixture was stirred for 2 h in an ice bath. The reaction mixture was poured into saturated $NaHCO_3$ solution (25 mL) and ice (25 g), and was stirred for 30 min. The organic phase was separated and the aqueous phase was extracted with $CH_2Cl_2$ (20 mL). The combined $CH_2Cl_2$ solution was washed with brine (20 mL), dried over anhydrous $MgSO_4$ and evaporated to dryness to afford a yellow solid. The crude product was purified by flash column chromatography on silica gel with EtOAc-hexane (1:2) as eluent to afford the titled compound (658 mg, 89%). Crystallization from EtOAc-hexane gave an analytically pure product.

IR (KBr): 1714, 1643, 1453 cm$^{-1}$; $^1$H NMR (CDCl$_3$/TMS): δ 1.24 (t, J=7.2 Hz, 3 H, OCH$_2$CH$_3$), 1.30 (d, J=6.9 Hz, 6 H, CH(CH$_3$)$_2$), 3.21 (septet, J=6.9 Hz, 1 H, CH(CH$_3$)$_2$), 3.67 (q, J=7.2 Hz, 2 H, OCH$_2$CH$_3$), 5.50 (s, 2 H, NCH$_2$O), 9.00 (br s, 1 H, NH); $^{13}$C NMR(CDCl$_3$): δ 15.04, 29.22, 65.41, 74.85, 118.61, 142.49, 150.22, 160.77

Preparative Example 2

Preparation of 6-chloro-1-(ethoxymethyl)-5-ethyluracil (a compound of the general formula (IV) wherein $R^1=C_2H$, $R^3=CH_3$ and $X=O$)

The titled compound was prepared in the same manner as described in Preparative Example 1 by using 6-chloro-5-ethyluracil in place of 6-chloro-5-isopropyluracil.

Yield: 93%; IR (KBr): 1722, 1667, 1455 cm$^{-1}$; $^1$H NMR (CDCl$_3$/TMS): δ 1.10 (t, J=7.4 Hz, 3 H, CH$_2$CH$_3$), 1.23 (t, J=7.1 Hz, 3 H, OCH$_2$CH$_3$), 2.56 (q, J=7.4 Hz, 2 H, CH$_2$CH$_3$), 3.67 (q, J=7.1 Hz, 2 H, OCH$_2$CH$_3$), 5.50 (s, 2 H, NCH$_2$O), 9.68 (br s, 1 H, NH) $^{13}$C NMR(CDCl$_3$): δ 12.20, 15.01, 20.08, 65.40, 74.75, 116.07, 143.09, 150.34, 161.50

Preparative Example 3

Preparation of 1-[(benzyloxy)methyl]-6-chloro-5-isopropyluracil (a compound of the general formula (IV) wherein $R^1=CH(CH_3)_2$, $R^3=Ph$ and $X=O$)

To a stirred suspension of 6-chloro-5-isopropyluracil (566 mg, 3.0 mmol) in anhydrous $CH_2Cl_2$ (9 mL) at room temperature under a nitrogen atmosphere was slowly added N,O-bis(trimethylsilyl)acetamide (1.41 g, 6.6 mmol, 1.72 mL) via a syringe and the mixture was stirred for an additional 2 h at room temperature. To the resulting clear reaction mixture at room temperature was added $Bu_4NI$ (11 mg, 0.03 mmol) in one portion followed by benzyl chloromethyl ether (593 mg, 3.6 mmol, 0.53 mL) and the mixture was refluxed in an oil bath for 2 h. The reaction mixture was cooled to room temperature and was poured into saturated $NaHCO_3$ solution (25 mL) and ice (25 g).

The mixture was stirred for 30 min, the organic phase was separated and the aqueous phase was extracted with $CH_2Cl_2$ (20 mL). The combined $CH_2Cl_2$ solution was washed with brine (20 mL), dried over anhydrous $MgSO_4$ and evaporated to dryness to afford a yellow solid. The crude product was purified by flash column chromatography on silica gel with EtOAc-hexane (1:2) as eluent to afford the titled compound (865 mg, 94%). Crystallization from EtOAc-hexane gave an analytically pure product.

IR (KBr): 1705, 1678, 1439 cm$^{-1}$; $^1$H NMR (CDCl$_3$/TMS): δ 1.27 (d, J=6.9 Hz, 6 H, CH(CH$_3$)$_2$), 3.20 (septet, J=6.9 Hz, 1 H, CH(CH$_3$)$_2$), 4.70 (s, 2 H, OCH$_2$Ph), 5.59 (s, 2 H, NCH$_2$O), 7.26–7.40 (m, 5 H, Ar H), 8.68 (br s, 1 H, NH); $^{13}$C NMR(CDCl$_3$): δ 19.52, 29.16, 72.09, 74.89, 118.69, 137.21, 142.26, 150.11, 160.50

Preparative Example 4

Preparation of 1-[(benzyloxy)methyl]-6-chloro-1-ethyluracil (a compound of the general formula (IV) wherein R$^1$=C$_2$H$_5$, R$^3$=Ph and X=O)

The titled compound was prepared in the same manner as described in Preparative Example 3 by using 6-chloro-5-ethyluracil in place of 6chloro-5-isopropyluracil.

Yield: 88%; IR (KBr): 1700, 1671, 1446 cm$^{-1}$; $^1$H NMR (CDCl$_3$/TMS): δ 1.08 (t, J=7.5 Hz, 3 H, CH$_2$CH$_3$), 2.52 (q, J=7.5 Hz, 2 H, CH$_2$CH$_3$), 4.70 (s, 2 H, OCH$_2$Ph), 5.58 (s, 2 H, NCH$_2$O), 7.26–7.34 (m, 5 H, Ar H), 9.50 (br s, 1 H, NH); $^{13}$C NMR(CDCl$_3$): δ 12.19, 20.24, 72.02, 74.74, 76.58, 116.16, 127.58, 127.94, 128.40, 137.13, 142.88, 150.25, 161.27

Preparative Example 5

Preparation of 1-(ethoxymethyl)-5-ethyl-2-thiouracil (a compound of the general formula (V) wherein R$^1$=C$_2$H$_5$, R$^3$=CH$_3$ and X=S)

A strirred suspension of 5-ethyl-2-thiouracil (9.00 g, 57.6 mmol) and (NH$_4$)$_2$SO$_4$ (1.20 g) in 1,1,1,3,3,3-hexamethyldisilazane (170 mL) was heated at reflux for 16 h under a nitrogen atmosphere. Volatile materials were evaporated in vacuo with protection against moisture. The residual oil was dissolved in MeCN (300 mL), and to the solution were added chloromethyl ethyl ether (6.53 g, 69.1 mmol, 6.4 mL) and CsI (15.00 g, 57.6 mmol). The mixture was heated at reflux for 2 h under a nitrogen atmosphere and allowed to cool to room temperature. The reaction mixture was poured into H$_2$O (300 mL) and then it was extracted with EtOAc (3×300 mL). The organic phase was washed with saturated NaHCO$_3$ solution (300 mL), dried over anhydrous MgSO$_4$ and concentrated to dryness. The residue was purified by flash column chromatography on silica gel with CHCl$_3$ as eluent and then crystallized from 2-propanol to give 4.35 g (35%) of the target compound.

IR (KBr): 1680 cm$^{-1}$; $^1$H NMR (CDCl$_3$TMS): δ 1.17 (t, J=7.5 Hz, 3 H, CH$_2$CH$_3$), 1.25 (t, J=7.1 Hz, 3 H, OCH$_2$CH$_3$), 2.42 (dq, J=0.9 Hz, J=7.5 Hz, 2 H, CH$_2$CH$_3$), 3.69 (q, J=7.1 Hz, 2 H, OCH$_2$CH$_3$), 5.61 (s, 2 H, NCH$_2$O), 7.26 (d, J=0.9 Hz, 1 H, H-6), 9.62 (br s, 1 H, NH)

Preparative Example 6

Preparation of 1-(ethoxymethyl)-5-isopropyl-2-thiouracil (a compound of the general formula (V) wherein R$_1$=CH(CH$_3$)$_2$, R$^3$=CH$_3$ and X=S)

The titled compound was prepared in the same manner as described in Preparative Example 5 by using 5-isopropyl-2-thiouracil in place of 5-ethyl-2-thiouracil.

Yield: 27%; IR (KBr): 1674 cm$^{-1}$; $^1$H NMR (CDCl$_3$/TMS): δ 1.19 (d, J=6.9 Hz, 6 H, CH(CH$_3$)$_2$), 1.25 (t, J=7.1 Hz, 3 H, OCH$_2$CH$_3$), 2.94 (septet, J=6.9 Hz, 1 H, CH(CH$_3$)$_2$), 3.69 (q, J=7.1 Hz, 2 H, OCH$_2$CH$_3$), 5.16 (s, 2 H, NCH$_2$O), 7.23 (s, 1 H, H-6), 9.49 (br s, 1 H, NH)

Preparative Example 7

Preparation of 1-[(benzyloxy)methyl]-5-ethyl-2-thiouracil (a compound of the general formula (V) wherein R$^1$=C$_2$H$_5$, R$^3$=C$_6$H$_5$ and X=S)

The titled compound was prepared in the same manner as described in Preparative Example 5 by using benzyl chloromethyl ether in place of chloromethyl ethyl ether.

Yield: 29%; IR (KBr): 3448, 1654 cm$^{-1}$; $^1$H NMR (CDCl$_3$/TMS): δ 1.13 (t, J=7.5 Hz, 3 H, CH$_2$CH$_3$), 2.37 (q, J=7.5 Hz, 2 H, CH$_2$CH$_3$), 4.72 (s, 2 H, CH$_2$Ph), 5.71 (s, 2 H, NCH$_2$O), 7.20 (s, 1 H, H-6), 7.25–7.45 (m, 5 H, Ar H), 9.37 (br s, 1 H, NH)

Preparative Example 8

Preparation of 1-[(benzyloxy)methyl]-5-isopropyl-2-thiouracil (a compound of the general formula (V) wherein R$^1$=CH(CH$_3$)$_2$, R$^3$=C$_6$H$_5$ and X=S)

The titled compound was prepared in the same manner as described in Preparative Example 5 by using 5-isopropyl-2-thiouracil and benzyl chloromethyl ether in place of 5-ethyl-2-thiouracil and chloromethyl ethyl ether, respectively.

Yield: 27%; IR (KBr): 3446, 1678 cm$^{-1}$; $^1$H NMR (CDCl$_3$/TMS): δ 1.15 (d, J=6.9 Hz, 6 H, CH(CH$_3$)$_2$), 2.90 (septet, J=6.9 Hz, 1 H, CH(CH$_3$)$_2$), 4.72 (s, 2 H, CH$_2$Ph), 5.72 (s, 2 H, NCH$_2$O), 7.17 (s, 1 H, H-6), 7.36 (m, 5 H, Ar H), 9.45 (br s, 1 H, NH)

Preparative Example 9

Preparation of 1-(ethoxymethyl)-5-ethyluracil (a compound of the general formula (V) wherein R$^1$=C$_2$H$_5$, R$^3$=CH$_3$ and X=O)

A suspension of 5-ethyluracil (3.50 g, 25.0 mmol) and N,O-bis(trimethylsilyl)acetamide (11.19 g, 55.0 mmol, 13.6 mL) in CH$_2$Cl$_2$ (30 mL) was stirred at room temperature for 2 h under a nitrogen atmosphere. To the resulting solution, Bu$_4$NI (93 mg, 0.25 mmol) and chloromethyl ethyl ether (2.84 g, 30.0 mmol, 2.8 mL) were added. The mixture was heated at reflux for 2 h and allowed to cool to room temperature. The reaction mixture was poured into saturated NaHCO$_3$ solution (10 mL) and ice (5 mL), and stirred for an additional 30 min. The organic phase was washed with brine (15 mL), dried over anhydrous MgSO$_4$ and concentrated to dryness. The residue was crystallized from EtOH to give 4.39 g (89%) of the target compound.

IR (KBr): 3218, 1694 cm$^{-1}$; $^1$H NMR (CDCl$_3$/TMS): δ 1.15 (t, J=7.5 Hz, 3 H, CH$_2$CH$_3$), 1.22 (t, J=7.1 Hz, 3 H, OCH$_2$CH$_3$), 2.38 (q, J=7.5 Hz, 2 H, CH$_2$CH$_3$), 3.61 (q, J=7.1 Hz, 2 H, OCH$_2$CH$_3$), 5.16 (s, 2 H, NCH$_2$O), 7.10 (s, 1 H, H-6), 9.41 (br s, 1 H, NH); $^{13}$C NMR(CDCl$_3$): δ 12.62, 14.89, 19.90, 64.99, 76.22, 117.36, 138.08, 151.20, 163.79

Preparative Example 10

Preparation of 1-(ethoxymethyl)-5-isopropyluracil (a compound of the general formula (V) wherein R$^1$=CH(CH$_3$)$_2$, R$^3$=CH$_3$ and X=O)

The titled compound was prepared in the same manner as described in Preparative Example 9 by using 5-isopropyluracil in place of 5-ethyluracil.

Yield: 90%; IR (KBr): 3230, 1698 cm$^{-1}$; $^1$H NMR (CDCl$_3$/TMS): δ 1.17 (d, J=6.9 Hz, 6 H, CH(CH$_3$)$_2$), 1.23 (t, J=7.1 Hz, 3 H, OCH$_2$CH$_3$), 2.92 (septet, J=6.9 Hz, 1 H, CH(CH$_3$)$_2$), 3.62 (q, J=7.1 Hz, 2 H, OCH$_2$CH$_3$), 5.16 (s, 2 H, NCH$_2$O), 7.07 (s, 1 H, H-6), 9.35 (br s, 1 H, NH) $^{13}$C NMR(CDCl$_3$): δ 6 14.90, 21.47, 25.72, 65.02, 76.31, 121.79, 137.19, 151.05, 163.39

Preparative Example 11

Preparation of 1-[(benzyloxy)methyl]-5-ethyluracil (a compound of the general formula (V) wherein R$^1$=C$_2$H$_5$, R$^3$=C$_6$H, and X=O)

The titled compound was prepared in the same manner as described in Preparative Example 9 by using benzyl chloromethyl ether in place of chloromethyl ethyl ether.

Yield: 83%; IR (KBr): 3446, 1702, 1660 cm$^{-1}$; $^1$H NMR (CDCl$_3$/TMS): δ 1.12 (t, J=7.5 Hz, 3 H, CH$_2$CH$_3$), 2.35 (q, J=7.5 Hz, 2 H, CH$_2$CH$_3$), 4.63 (s, 2 H, CH$_2$Ph), 5.23 (s, 2 H, NCH$_2$O), 7.05 (s, 1 H, H-6), 7.30–7.40 (m, 5 H, Ar H), 8.94 (br s, 1 H, NH) $^{13}$C NMR(CDCl$_3$): δ 12.56, 19.86, 71.59, 76.06, 117.38, 127.86, 128.10, 128.47, 136.73, 138.06, 151.18, 163.70

Preparative Example 12

Preparation of 1-[(benzyloxy)methyl]-5-isopropyluracil (a compound of the general formula (V) wherein R$^1$=CH(CH$_3$)$_2$, R$^3$=C$_6$H$_5$ and X=O)

The titled compound was prepared in the same manner as described in Preparative Example 9 by using 5-isopropyluracil and benzyl chloromethyl ether in place of 5-ethyluracil and chloromethyl ethyl ether, respectively.

Yield: 96%; IR (KBr): 3404, 1708, 1654 cm$^{-1}$; $^1$H NMR (CDCl$_3$/TMS): δ 1.15 (d, J=6.9 Hz, 6 H, CH(CH$_3$)$_2$), 2.89 (septet, J=6.9 Hz, 1 H, CH(CH$_3$)$_2$), 4.64 (s, 2 H, CH$_2$Ph), 5.23 (s, 2 H, NCH$_2$O), 7.01 (s, 1 H, H-6), 7.30–7.40 (m, 5 H, Ar H), 8.64 (br s, 1 H, NH); $^{13}$C NMR(CDCl$_3$): δ 21.45, 25.70, 71.68, 76.20, 121.81, 127.88, 128.14, 128.51, 136.75, 137.20, 150.94, 163.20

Preparative Example 13

Preparation of 1-[[2-(tert-butyldimethylsiloxy)ethoxy]methyl]-5-ethyl-2-thiouracil (a compound of the general formula (VI) wherein R$^1$=C$_2$H$_5$, W=(tert-butyldimethylsiloxy)-methyl and X=S)

A stirred suspension of 5-ethyl-2-thiouracil (6.00 g, 38.4 mmol) and (NH$_4$)$_2$SO$_4$ (0.80 g) in 1,1,1,3,3,3-hexamethyldisilazane (110 mL) was heated at reflux for 16 h under a nitrogen atmosphere. Volatile materials were evaporated in vacuo with protection against moisture. The residual oil was dissolved in MeCN (300 mL), and to this solution cooled to −60° C. were added [2-(trimethylsiloxy)ethoxy]methyl iodide, which was in situ generated from 1,3-dioxolane (3.41 g, 46.1 mmol, 3.2 mL) and iodotrimethylsilane (8.45 g, 42.2 mmol, 6.0 mL) in cyclohexene (20 mL) at −78° C. for 15 min under a nitrogen atmosphere, and CsI (10.00 g, 38.4 mmol). The mixture was slowly allowed to warm to room temperature and stirred for 3 h under a nitrogen atmosphere. The reaction mixture was poured into saturated NaHCO$_3$ solution (100 mL) and it was then extracted by using continuous extractor with CH$_2$Cl$_2$. The CH$_2$Cl$_2$ was solution dried over anhydrous MgSO$_4$ and evaporated to dryness to give 3.02 g of a residue. To a stirred solution of the residue in DMF (40 mL) were added imidazole (1.07 g, 15.74 mmol) and tert-butyldimethylsilyl chloride (2.37 g, 15.74 mmol), and the mixture was stirred at room temperature for 16 h. The reaction mixture was poured into H$_2$O (100 mL) and it was then extracted with EtOAc (3×100 mL). The organic phase was washed with brine, dried over anhydrous MgSO$_4$, and evaporated to dryness. The residue was purified by flash column chromatography on silica gel with EtOAc-hexane (1:3) as eluent to give 4.74 g (36%) of the target compound.

IR (KBr): 3230, 1698 cm$^{-1}$; $^1$H NMR (CDCl$_3$/TMS): δ 0.08 (s, 6 H, Si(CH$_3$)$_2$), 0.90 (s, 9 H, SiC(CH$_3$)$_3$), 1.16 (t, J=7.5 Hz, 3 H, CH$_2$CH$_3$), 2.41 (q, J=7.5 Hz, 2 H, CH$_2$CH$_3$), 3.72 (m, 2 H, CH$_2$OSi), 3.79 (m, 2 H, OCH2), 5.66 (s, 2 H, NCH$_2$O), 7.29 (s, 1 H, H-6), 9.57 (br s, 1 H, NH)

Preparative Example 14

Preparation of 1-[[2-(tert-butyldimethylsiloxy)ethoxy]methyl]-5-isopropyl-2-thiouracil (a compound of the general formula (VI) wherein R$^1$=CH(CH$_3$)$_2$, W=(tert-butyldimethylsiloxy)methyl and X=S)

The titled compound was prepared in the same manner as described in Preparative Example 13 by using 5-isopropyl-2-thiouracil in place of 5-ethyl-2-thiouracil.

Yield: 33%; IR (KBr): 3226, 1694 cm$^{-1}$; $^1$H NMR (CDCl$_3$/TMS): δ 0.08 (s, 6 H, Si(CH$_3$)$_2$), 0.90 (s, 9 H, SiC(CH$_3$)$_3$), 1.18 (d, J=6.9 Hz, 6 H, CH(CH$_3$)$_2$), 2.93 (septet, J=6.9 Hz, 1 H, CH(CH$_3$)$_2$), 3.73 (m, 2 H, CH$_2$OSi), 3.79 (m, 2 H, OCH$_2$), 5.67 (s, 2 H, NCH$_2$O), 7.24 (s, 1 H, H-6), 9.61 (br s, 1 H, NH)

Preparative Example 15

Preparation of 1-[[2-(tert-butyldimethylsiloxy)ethoxy]methyl]-5-ethyluracil (a compound of the general formula (VI) wherein R$^1$=C$_2$H$_5$, W=(tert-butyldimethylsiloxy)-methyl and X=O)

A suspension of 5-ethyluracil (4.50 g, 32.1 mmol) and N,O-bis(trimethylsilyl)acetamide (14.37 g, 70.6 mmol, 17.5 mL) in CH$_2$Cl$_2$ (40 mL) was stirred at room temperature for 2 h under a nitrogen atmosphere. To the resulting solution cooled to −60° C. was added [2-(trimethylsiloxy)ethoxy]methyl iodide which was in situ generated from 1,3-dioxolane (2.85 g, 38.5 mmol, 2.7 mL) and iodotrimethylsilane (7.07 g, 35.3 mmol, 5.0 mL) in cyclohexene (20 mL) at −78° C. for 15 min under a nitrogen atmosphere. The mixture was allowed to warm to room temperature over 30 min and stirred for 3 h under a nitrogen atmosphere. The reaction mixture was poured into saturated NaHCO$_3$ solution (80 mL) and it was then extracted by using continuous extractor with CH$_2$Cl$_2$. The CH$_2$Cl$_2$ solution was dried over anhydrous MgSO$_4$ and evaporated to dryness to give 6.20 g of a residue. To a stirred solution of the residue in DMF (80 mL) were added imidazole (2.62 g, 38.5 mmol) and tert-butyldimethylsilyl chloride (5.81 g, 38.5 mmol), and the mixture was stirred at room temperature for 16 h. The reaction mixture was poured into H$_2$O (200 mL) and it was then extracted with EtOAc (3×200 mL). The organic phase was washed with brine, dried over anhydrous MgSO$_4$, and evaporated to dryness. The residue was purified by flash column chromatography on silica gel with EtOAc-hexane (1:1) as eluent to give 7.45 g (71%) of the target compound.

IR (KBr): 3231, 1689 cm$^{-1}$; $^1$H NMR (CDCl$_3$/TMS): δ 0.06 (s, 6 H, Si(CH$_3$)$_2$), 0.89 (s, 9 H, SiC(CH$_3$)$_3$), 1.14 (t, J=7.4 Hz, 3 H, CH$_2$CH$_3$), 2.37 (q, J=7.4 Hz, 2 H, CH$_2$CH$_3$), 3.65 (m, 2 H, CH$_2$OSi), 3.77 (m, 2 H, OCH$_2$), 5.21 (s, 2 H, NCH$_2$O), 7.11 (s, 1 H, H-6), 9.50 (br s, 1 H, NH); $^{13}$C NMR (CDCl$_3$): δ −5.33, 12.60, 18.29, 19.90, 25.84, 62.36, 71.01, 76.77, 117.29, 138.12, 151.16, 163.79

Preparative Example 16

Preparation of 1-[[2-(tert-butyldimethylsiloxy)ethoxy]methyl]-5-isopropyluracil (a compound of the general formula (VI) wherein R$^1$=CH(CH$_3$)$_2$, W=(tert-butyldimethylsiloxy)methyl and X=O)

The titled compound was prepared in the same manner as described in Preparative Example 15 by using 5-isopropyluracil in place of 5-ethyluracil.

Yield: 87%; IR (KBr): 3270, 3221, 1688 cm$^{-1}$; $^1$H NMR (CDCl$_3$/TMS): δ 0.07 (s, 6 H, Si(CH$_3$)$_2$), 0.89 (s, 9 H, SiC(CH$_3$)$_3$), 1.16 (d, J=6.9 Hz, 6 H, CH(CH$_3$)$_2$), 2.92 (septet, J=6.9 Hz, 1 H, CH(CH$_3$)$_2$), 3.65 (m, 2 H, CH$_2$OSi), 3.77 (m, 2 H, OCH$_2$), 5.21 (s, 2 H, NCH$_2$O), 7.07 (s, 1 H, H-6), 9.18 (br s, 1 H, NH); $^{13}$C NMR(CDCl$_3$): δ −5.28, 18.33, 21.46, 25.75, 25.89, 62.42, 71.11, 76.94, 121.74, 137.29, 150.95, 163.31

Preparative Example 17

Preparation of 3,3-(dimethylthio)-2-ethylacrylic acid (a compound of the general formula (IX) wherein R$^1$=C$_2$H$_5$)

A mixture of ethyl 3,3-(dimethylthio)-2-ethylacrylate (300 mmol) and 2N KOH (300 mL) in EtOH (300 mL) was heated under reflux for 3 h. The reaction mixture was concentrated to remove EtOH and poured into H$_2$O (300 mL). The aqueous phase was washed with Et$_2$O (200 mL×2), acidified with concentrated HCl to pH 3, and extracted with Et$_2$O (200 mL×3). The combined ethereal solution was washed with brine, dried over anhydrous MgSO$_4$, filtered, and evaporated to dryness. The residue was crystallized from hexane to give the titled compound as white crystals.

Yield: 86%; IR (KBr): 1690 (CO) cm$^{-1}$; $^1$H NMR(CDCl$_3$/TMS): δ 1.10 (t, J=7.5 Hz, 3 H, CH$_2$CH$_3$), 2.37 (s, 6 H, 2 SCH$_3$), 2.69 (q, J=7.5 Hz, 2 H, CH$_2$CH$_3$), 11.48 (br s, 1 H, COOH)

Preparative Example 18

Preparation of 3,3-(dimethylthio)-2-isopropylacrylic acid (a compound of the general formula (IX) wherein R$^1$=CH(CH$_3$)$_2$)

The titled compound was prepared in the similar manner as described in Preparative Example 17 by using ethyl 3,3-(dimethylthio)-2-isopropylacrylate in place of ethyl 3,3-(dimethylthio)-2-ethylacrylate.

Yield: 82%; IR (KBr): 1690 (CO) cm$^{-1}$; $^1$H NMR (CDCl$_3$/TMS): δ 1.15 (d, J=6.9 Hz, 6 H, 2 CH$_3$), 2.29 (s, 3 H, SCH$_3$), 2.34 (s, 3 H, SCH$_3$), 3.34 (septet, J=6.9 Hz, 1 H, CH)

Preparative Example 19

Preparation of 3,3-(dimethylthio)-2-ethylacryloyl chloride (a compound of the general formula (X) wherein R$^1$=C$_2$H$_5$)

To a stirred solution of 3,3-(dimethylthio)-2-ethylacrylic acid (100 mmol) in anhydrous benzene (100 mL) were added oxalyl chloride (10.5 mL, 120 mmol) dropwise and 3 drops of DMF at 0 ° C. under a nitrogen atmosphere. The mixture was stirred at room temperature for 3 h and evaporated to dryness. The residue was distilled in vacuo to give the titled compound as a brick red oil.

Yield: 91%; IR (neat): 1786 (CO) cm$^{-1}$; $^1$H NMR (CDCl$_3$/TMS): δ 1.14 (t, J=7.5 Hz, 3 H, CH$_2$CH$_3$), 2.37 (s, 3 H, SCH$_3$), 2.40 (s, 3 H, SCH$_3$), 2.72 (q, J=7.5 Hz, 2 H, CH$_2$CH$_3$)

Preparative Example 20

Preparation of 3,3-(dimethylthio)-2-isopropylacryloyl chloride (a compound of the general formula (X) wherein R$^1$=CH(CH$_3$)$_2$)

The titled compound was prepared in the same manner as described in Preparative Example 19 by using 3,3-(dimethylthio)-2-isopropylacrylic acid in place of 3,3-(dimethylthio)-2-ethylacrylic acid.

Yield: 91%; IR (neat): 1786 (CO) cm$^{-1}$; $^1$H NMR(CDCl$_3$/TMS): δ 1.18 (d, J=6.9 Hz, 6 H, 2 CH$_3$), 2.32 (s, 3 H, SCH$_3$), 2.36 (s, 3 H, SCH$_3$), 3.32 (septet, J=6.9 Hz, 1 H, CH)

Preparative Example 21

Preparation of N-butyl-N'-[3,3-(dimethylthio)-2-ethylacryloyl]urea (a compound of the general formula (XIa) wherein R$^1$=C$_2$H$_5$, R$^3$=CH$_3$ and X=O)

A mixture of 3,3-(dimethylthio)-2-ethylacryloyl chloride (3.50 g, 16.6 mmol) and AgOCN (2.61 g, 17.4 mmol) in anhydrous benzene (30 mL) was heated under reflux for 30 min under a nitrogen atmosphere in the dark to generate isocyanate in situ and cooled to −78° C. To this mixture was added butylamine (1.81 mL, 18.3 mmol) in anhydrous benzene (10 mL) in a dropwise manner. The mixture was allowed to warm to room temperature over 30 min and filtered through a pad of Celite, and the filtrate was again filtered using a millipore filter (0.22 mm). The filtrate was evaporated to dryness and the residue was purified by flash column chromatography on silica gel with EtOAc-hexane (1:6) as eluent to give 4.21 g of the titled compound.

Yield: 87%; IR (KBr): 1665, 1690 (CO) cm$^{-1}$; $^1$H NMR (CDCl$_3$/TMS): δ 0.94 (t, J=7.2 Hz, 3 H, NCH$_2$CH$_2$CH$_2$CH$_3$), 1.07 (t, J=7.5 Hz, 3 H, CH$_2$CH$_3$), 1.39 (m, 2 H, NCH$_2$CH$_2$CH$_2$), 1.58 (m, 2 H, NCH2CH$_2$), 2.31 (s, 3 H, SCH$_3$), 2.34 (s, 3 H, SCH$_3$), 2.62 (q, J=7.5 Hz, 2 H, CH$_2$CH$_3$), 3.31 (m, 2 H, NCH$_2$), 8.27 (br s, 2 H, 2 NH); $^{13}$C NMR (CDCl$_3$): δ 12.90, 13.71, 16.37, 17.71, 20.14, 27.22, 30.23, 45.51, 139.02, 142.35, 168.94, 179.52

Preparative Example 22

Preparation of N-[3,3-(dimethylthio)-2-ethylacryloyl]-N'-(3-phenylpropyl)urea (a compound of the general formula (XIa) wherein R$^1$=C$_2$H$_5$, R$^3$=Ph and X=O)

The titled compound was prepared in the same manner as described in Preparative Example 21 by using 3-phenyl-1-propylamine in place of butylamine.

Yield: 91%; IR (KBr): 1662, 1698 (CO) cm$^{-1}$; $^1$H NMR (CDCl$_3$/TMS): δ 1.06 (t, J=7.5 Hz, 3 H, CH$_2$CH$_3$), 1.92 (quintet, J=7.5 Hz, 2 H, NCH$_2$CH$_2$), 2.30 (s, 3 H, SCH$_3$), 2.32 (s, 3 H, SCH$_3$), 2.57–2.73 (m, 4 H, CH$_2$Ph and CH$_2$CH$_3$), 3.33 (dd, J=12.9 Hz, J=6.9 Hz, 2 H, NCH$_2$), 7.12–7.33 (m, 5 H, Ar H), 8.37 (br s, 1 H, NH), 8.49 (br s, 1 H, NH); $^{13}$C NMR(CDCl$_3$): δ 12.83, 16.34, 17.46, 27.07, 31.09, 33.11, 39.37, 125.91, 128.34, 128.38, 136.49, 141.29, 143.91, 153.90, 170.50

Preparative Example 23

Preparation of N-butyl-N'-[3,3-(dimethylthio)-2-isopropylacryloyl]urea (a compound of the general formula (XIa) wherein R$^1$=CH(CH$_3$)$_2$, R$^3$=CH$_3$ and X=O)

The titled compound was prepared in the same manner as described in Preparative Example 21 by using 3,3-(dimethylthio)-2-isopropylacryloyl chloride in place of 3,3-(dimethylthio)-2-ethylacryloyl chloride.

Yield: 84%; IR (KBr): 1674, 1696 (CO) cm$^{-1}$; $^1$H NMR (CDCl$_3$/TMS): δ 0.94 (t, J=7.2 Hz, 3 H, NCH$_2$CH$_2$CH$_2$CH$_3$), 1.11 (d, J=6.9 Hz, 6 H, CH(CH$_3$)$_2$), 1.38 (m, 2 H, NCH$_2$CH$_2$CH$_2$), 1.57 (m, 2 H, NCH$_2$CH$_2$), 2.26 (s, 3 H, SCH$_3$), 2.32 (s, 3 H, SCH$_3$), 3.23–3.40 (m, 3 H, NCH$_2$ and CH(CH$_3$)$_2$), 8.32 (br s, 1 H, NH), 8.83 (br s, 1 H, NH); $^{13}$C NMR (CDCl$_3$): δ 13.75, 16.25, 17.31, 20.09, 21.12, 31.58, 32.34, 39.61, 133.79, 149.14, 153.83, 169.59

Preparative Example 24

Preparation of N-[3,3-(dimethylthio)-2-isopropylacryloyl]-N'-(3-phenylpropyl)urea (a compound of the general formula (XIa) wherein R$^1$=CH(CH$_3$)$_2$, R$^3$=Ph and X=O)

The titled compound was prepared in the same manner as described in Preparative Example 21 by using 3,3-(dimethylthio)-2-isopropylacryloyl chloride and 3-phenyl-1-propylamine in place of 3,3-(dimethylthio)-2-ethylacryloyl chloride and butylamine, respectively.

Yield: 88%; IR (KBr): 1675, 1695 (CO) cm$^{-1}$; $^1$H NMR (CDCl$_3$/TMS): δ 1.11 (d, J=6.9 Hz, 6 H, CH(CH$_3$)$_2$) 1.92 (quintet, J=7.5 Hz, 2 H, NCH$_2$CH$_2$), 2.26 (s, 3 H, SCH$_3$), 2.31 (s, 3 H, SCH$_3$), 2.69 (t, J=7.8 Hz, 2 H, CH$_2$Ph), 3.25–3.40 (m, 3 H, NCH$_2$ and CH(CH$_3$)$_2$), 7.15–7.33 (m, 5 H, Ar H), 8.38 (br s, 1 H, NH), 8.58 (br s, 1 H, NH); $^{13}$C NMR(CDCl$_3$): δ 16.24, 17.35, 21.14, 31.10, 32.33, 33.10, 39.36, 125.93, 128.36, 128.40, 133.99, 141.30, 148.99, 153.71, 169.57

Preparative Example 25

Preparation of N-[3,3-(dimethylthio)-2-ethylacryloyl]-N'-(4-hydroxybutyl) thiourea (a compound of the general formula (XIb) wherein R$^1$=C$_2$H$_5$, R$^3$=CH$_2$OH and X=S)

A mixture of 3,3-(dimethylthio)-2-ethylacryloyl chloride (5.20 g, 24.7 mmol) and NH$_4$SCN (1.97 g, 25.9 mmol) in anhydrous benzene (30 mL) was heated under reflux for 30 min under a nitrogen atmosphere in the dark to generate thioisocyanate in situ and cooled to 0° C. To this mixture was added 4-amino-1-butanol (2.50 mL, 27.2 mmol) in anhydrous benzene (10 mL) in a dropwise manner. After stirred at room temperature for 1 h, the mixture was poured into H$_2$O (40 mL) and extracted with EtOAc (50 mL×3). The combined organic phase was washed with brine (50 mL), dried over anhydrous MgSO$_4$, filtered, and evaporated to dryness. The residue was purified by flash column chromatography on silica gel with EtOAc-hexene (1:2) as eluent to give 6.39 g of the titled compound.

Yield: 80%; IR (KBr): 1663 (CO), 3385 (OH) cm$^{-1}$; $^1$H NMR (CDCl$_3$/TMS): δ 1.07 (t, J=7.5 Hz, 3 H, CH$_2$CH$_3$), 1.55 (br s, 1 H, OH), 1.67 (m, 2 H, NCH$_2$CH$_2$CH$_2$), 1.82 (m, 2 H, NCH$_2$CH$_2$), 2.36 (s, 6 H, 2 SCH$_3$), 2.63 (q, J=7.5 Hz, 2 H, CH$_2$CH$_3$), 3.62–3.80 (m, 4 H, NCH$_2$ and CH$_2$OH), 8.96 (br s, 1 H, NH), 10.47 (br s, 1 H, NH) $^{13}$C NMR(CDCl$_3$): δ 12.87, 16.34, 17.65, 24.65, 27.18, 29.76, 45.29, 62.11, 138.94, 142.31, 169.01, 179.70

Preparative Example 26

Preparation of N-butyl-N'-[3,3-(dimethylthio)-2-ethylacryloyl]thiourea (a compound of the general formula (XIb) wherein R$^1$=C$_2$H$_5$, R$^3$=CH$_3$ and X=S)

The titled compound was prepared in the same manner as described in Preparative Example 25 by using butylamine in place of 4-amino-1-butanol.

Yield: 85%; IR (KBr): 1671 (CO) cm$^{-1}$; $^1$H NMR (CDCl$_3$/TMS): δ 0.97 (t, J=7.2 Hz, 3 H, NCH$_2$CH$_2$CH$_2$CH$_3$), 1.07 (t, J=7.5 Hz, 3 H, CH$_2$CH$_3$), 1.43 (m, 2 H, NCH$_2$CH$_2$CH$_2$), 1.68 (m, 2 H, NCH$_2$CH$_2$), 2.35 (s, 3 H, SCH$_3$), 2.36 (s, 3 H, SCH$_3$), 2.63 (q, J=7.5 Hz, 2 H, CH$_2$CH$_3$), 3.66 (m, 2 H, NCH$_2$), 9.15 (br s, 1 H, NH), 10.43 (br s, 1 H, NH); $^{13}$C NMR(CDCl$_3$): δ 12.90, 13.71, 16.37, 17.70, 20.14, 27.22, 30.24, 45.50, 138.99, 142.38, 168.96, 179.54

Preparative Example 27

Preparation of N-[3,3-(dimethylthio)-2-isopropylacryloyl]-N'-(4-hydroxybutyl) thiourea (a compound of the general formula (XIb) wherein R$^1$=CH(CH$_3$)$_2$, R$^3$=CH$_2$OH and X=S)

The titled compound was prepared in the same manner as described in Preparative Example 25 by using 3,3-(dimethylthio)-2-isopropylacryloyl chloride in place of 3,3-(dimethylthio)-2-ethylacryloyl chloride.

Yield: 77%; IR (KBr): 1666 (CO), 3253 (OH) cm$^{-1}$; $^1$H NMR(CDCl$_3$TMS): δ 1.13 (d, J=6.9 Hz, 6 H, CH(CH$_3$)$_2$), 1.60–1.73 (m, 2 H, NCH$_2$CH$_2$CH$_2$), 1.82 (m, 2 H, NCH$_2$CH$_2$), 2.31 (s, 3 H, SCH$_3$), 2.35 (s, 3 H, SCH$_3$), 3.33 (septet, J=6.9 Hz, 1 H, CH(CH$_3$)$_2$), 3.64–3.76 (m, 4 H, NCH$_2$ and CH$_2$OH), 8.84 (br s, 1 H, NH), 10.46 (br s, 1 H, NH) $^{13}$C NMR (CDCl$_3$): δ 16.19, 17.41, 21.08, 24.67, 29.79, 32.54, 45.34, 62.18, 135.71, 147.80, 168.56, 179.60

Preparative Example 28

Preparation of N-butyl-N'-[3,3-(dimethylthio)-2-isopropylacryloyl]thiourea (a compound of the general formula (XIb) wherein R$^1$=CH(CH$_3$)$_2$, R$^3$=CH$_3$ and X=S)

The titled compound was prepared in the same manner as described in Preparative Example 25 by using 3,3-(dimethylthio)-2-isopropylacryloyl chloride and butylamine in place of 3,3-(dimethylthio)-2-ethylacryloyl chloride and 4-amino-1-butanol, respectively.

Yield: 81%; IR (KBr): 1670 (CO) cm$^{-1}$; $^1$H NMR (CDCl$_3$/TMS): δ 0.97 (t, J=7.4 Hz, 3 H, NCH$_2$CH$_2$CH$_2$CH$_3$), 1.13 (d, J=6.9 Hz, 6 H, CH(CH$_3$)$_2$), 1.43 (m, 2 H, NCH$_2$CH$_2$CH$_2$), 1.69 (m, 2 H, NCH$_2$CH$_2$), 2.31 (s, 3 H, SCH$_3$), 2.35 (s, 3 H, SCH$_3$), 3.33 (septet, J=6.9 Hz, 1 H, CH(CH$_3$)$_2$), 3.66 (m, 2 H, NCH$_2$), 8.80 (br s, 1 H, NH), 10.40 (br s, 1 H, NH) $^{13}$C NMR(CDCl$_3$): δ 13.73, 16.19, 17.40, 20.14, 21.08, 30.22, 32.54, 45.51, 135.65, 147.85, 168.57, 179.43

Preparative Example 29

Preparation of 1-butyl-5-ethyl-6-(methylthio)uracil (a compound of the general formula (XII) wherein R$^1$=C$_2$H$_5$ and R$^3$=CH$_3$)

A stirred suspension of N-butyl-N'-[3,3-(dimethylthio)-2-ethylacryloyl]urea (0.50 g, 1.72 mmol) and methanesulfonic acid (25.0 mg, 0.26 mmol) in AcOH (10 mL) was heated at 80° C. for 1 h. The reaction mixture was evaporated to dryness and the residue was dissolved in CH$_2$Cl$_2$ (50 mL). The CH$_2$Cl$_2$ solution was washed with saturated NaHCO$_3$ solution (25 mL) and brine (25 mL), dried over anhydrous MgSO$_4$, filtered, and evaporated to dryness. The residue was purified by flash column chromatography on silica gel with EtOAc-hexane (1:3) as eluent to give 0.40 g of the titled compound.

Yield: 96%; IR (KBr): 1663, 1682 (CO) cm$^{-1}$; $^1$H NMR (CDCl$_3$/TMS): δ 0.96 (t, J=7.4 Hz, 3 H, NCH$_2$CH$_2$CH$_2$CH$_3$), 1.13 (t, J=7.5 Hz, 3 H, CH$_2$CH$_3$), 1.38 (m, 2 H, NCH$_2$CH$_2$CH$_2$), 1.65 (m, 2 H, NCH$_2$CH$_2$), 2.41 (s, 3 H, SCH$_3$), 2.71 (q, J=7.5 Hz, 2 H, CH$_2$CH$_3$), 4.13 (t, J=7.8 Hz, 2 H, NCH$_2$), 8.66 (br s, 1 H, NH) $^{13}$C NMR (CDCl$_3$): δ 13.73, 14.07, 19.88, 20.08, 22.23, 31.47, 46.53, 124.01, 149.20, 150.74, 162.10

Preparative Example 30

Preparation of 5-ethyl-6-(methylthio)-1-(3-phenylpropyl)uracil (a compound of the general formula (XII) wherein R$^1$=C$_2$H$_5$ and R$^3$=Ph)

The titled compound was prepared in the same manner as described in Preparative Example 29 by using N-[3,3-(dimethylthio)-2-ethylacryloyl]-N'-(3-phenylpropyl)urea in place of N-butyl-N'-[3,3-(dimethylthio)-2-ethylacryloyl] urea.

Yield: 93%; IR (KBr): 1667 (CO) cm$^{-1}$; $^1$H NMR (CDCl$_3$/TMS): δ 1.11 (t, J=7.5 Hz, 3 H, CH$_2$CH$_3$), 2.03 (tt, J=7.8 Hz, J=7.5 Hz, 2 H, NCH$_2$CH$_2$), 2.32 (s, 3 H, SCH$_3$), 2.67 (t, J=7.5 Hz, 2 H, CH$_2$Ph), 2.70 (q, J=7.5 Hz, 2 H, CH$_2$CH$_3$), 4.16 (t, J=7.8 Hz, 2 H, NCH$_2$), 7.19–7.31 (m, 5 H, Ar H), 8.90 (br s, 1 H, NH); $^{13}$C NMR (CDCl$_3$): δ 14.05, 19.97, 22.24, 30.52, 32.88, 46.36, 124.10, 126.06, 128.26, 128.39, 140.76, 149.00, 150.61, 161.86

Preparative Example 31

Preparation of 1-butyl-5-isopropyl-6-(methylthio)uracil (a compound of the general formula (XII) wherein R$^1$=CH(CH$_3$)$_2$ and R$^3$=CH$_3$)

The titled compound was prepared in the same manner as described in Preparative Example 29 by using N-butyl-N'-[3,3-(dimethylthio)-2-isopropylacryloyl]urea in place of N-butyl-N'-[3,3-(dimethylthio)-2-ethylacryloyl]urea.

Yield: 84%; IR (KBr): 1646, 1699 (CO) cm$^{-1}$; $^1$H NMR (CDCl$_3$/TMS): δ 0.96 (t, J=7.4 Hz, 3 H, NCH$_2$CH$_2$CH$_3$), 1.33 (d, J=6.9 Hz, 6 H, CH(CH$_3$)$_2$), 1.39 (m, 2 H, NCH$_2$CH$_2$CH$_2$), 1.64 (m, 2 H, NCH$_2$CH$_2$), 2.40 (s, 3 H, SCH$_3$), 3.54 (septet, J=6.9 Hz, 1 H, CH(CH$_3$)$_2$), 4.15 (t, J=7.8 Hz, 2 H, NCH$_2$), 8.77 (br s, 1 H, NH) $^{13}$C NMR (CDCl$_3$): δ 13.75, 19.88, 20.25, 20.55, 31.59, 31.70, 46.66, 126.39, 149.13, 150.58, 161.20

Preparative Example 32

Preparation of 5-isopropyl-6-(methylthio)-1-(3-phenylpropyl)uracil (a compound of the general formula (XII) wherein R$^1$=CH(CH$_3$)$_2$ and R$^3$=Ph)

The titled compound was prepared in the same manner as described in Preparative Example 29 by using N-[3,3-(dimethylthio)-2-isopropylacryloyl]-N'-(3-phenylpropyl)urea in place of N-butyl-N'-[3,3-(dimethylthio)-2-ethylacryloyl]urea.

Yield: 86%; IR (KBr): 1682, 1694 (CO) cm$^{-1}$; $^1$H NMR (CDCl$_3$/TMS): δ 1.31 (d, J=6.9 Hz, 6 H, CH(CH$_3$)$_2$), 2.01 (tt, J=7.8 Hz, J=7.7 Hz, 2 H, NCH$_2$CH$_2$), 2.32 (s, 3 H, SCH$_3$), 2.70 (t, J=7.7 Hz, 2 H, CH$_2$Ph), 3.51 (septet, J=6.9 Hz, 1 H, CH(CH$_3$)$_2$), 4.18 (t, J=7.8 Hz, 2 H, NCH$_2$), 7.16–7.31 (m, 5 H, Ar H), 8.55 (br s, 1 H, NH); $^{13}$C NMR (CDCl$_3$): δ 20.16, 20.53, 30.71, 31.68, 32.88, 46.49, 126.05, 126.53, 128.26, 128.38, 140.82, 148.89, 150.51, 161.04

Preparative Example 33

Preparation of 1-butyl-5-ethyl-6-(methylsulfonyl)uracil (a compound of the general formula (XIII) wherein R$^1$=C$_2$H$_5$ and R$^3$=CH$_3$)

A mixture of 1-butyl-5-ethyl 6-(methylthio)uracil (1.50 g, 6.2 mmol) and 3-chloroperoxybenzoic acid (85%, 6.29 g, 31.0 mmol) in benzene (50 mL) was heated under reflux for 16 h. The reaction mixture was evaporated to dryness and the residue was dissolved in H$_2$O (50 mL). The aqueous phase was extracted with EtOAc (50 mL×3). The combined EtOAc solution was washed with saturated NaHCO$_3$ solution (50 mL) and brine (50 mL), dried over anhydrous MgSO$_4$, filtered, and evaporated to dryness. The residue was purified by flash column chromatography on silica gel with EtOAc-hexane (1:2) as eluent to give 1.67 g of the titled compound.

Yield: 98%; IR (KBr): 1149 (SO$_2$), 1688 (CO) cm$^{-1}$; $^1$H NMR (CDCl$_3$/TMS): δ 0.95 (t, J=7.4 Hz, 3 H, NCH$_2$CH$_2$CH$_3$), 1.19 (t, J=7.2 Hz, 3 H, CH$_2$CH$_3$), 1.36 (m, 2 H, NCH$_2$CH$_2$CH$_2$), 1.72 (m, 2 H, NCH$_2$CH$_2$), 2.90 (q, J=7.2 Hz, 2 H, CH$_2$CH$_3$), 3.23 (s, 3 H, SO$_2$CH$_3$), 4.21 (t, J=7.8 Hz, 2 H, NCH$_2$), 9.17 (br s, 1 H, NH) $^{13}$C NMR (CDCl$_3$): δ 13.62, 14.35, 19.87, 20.42, 31.55, 45.32, 47.61, 124.52, 147.94, 150.10, 162.07

Preparative Example 34

Preparation of 5-ethyl-6-(methylsulfonyl)-1-(3-phenylpropyl)uracil (a compound of the general formula (XIII) wherein R$^1$=C$_2$H$_5$ and R$^3$=Ph)

The titled compound was prepared in the same manner as described in Preparative Example 33 by using 5-ethyl-6-(methylthio)-1-(3-phenylpropyl)uracil in place of 1-butyl-5-ethyl-6-(methylthio)uracil.

Yield: 93%; IR (KBr): 1150 (SO$_2$), 1690 (CO) cm$^{-1}$; $^1$H NMR (CDCl$_3$/TMS): δ 1.17 (t, J=7.4 Hz, 3 H, CH$_2$CH$_3$), 2.10 (tt, J=7.8 Hz, J=7.7 Hz, 2 H, NCH$_2$CH$_2$), 2.69 (t, J=7.7 Hz, 2 H, CH$_2$Ph), 2.86 (q, J=7.4 Hz, 2 H, CH$_2$CH$_3$), 3.10 (s, 3 H, SO$_2$CH$_3$), 4.23 (t, J=7.8 Hz, 2 H, NCH$_2$), 7.18–7.33 (m, 5 H, Ar H), 9.01 (br s, 1 H, NH); $^{13}$C NMR (CDCl$_3$): δ 14.30, 20.43, 30.70, 32.82, 45.13, 47.46, 124.66, 126.11, 128.35, 128.43, 140.59, 147.80, 150.21, 162.15

Preparative Example 35

Preparation of 1-butyl-5-isopropyl-6-(methylsulfonyl)uracil (a compound of the general formula (XIII) wherein R$^1$=CH(CH$_3$)$_2$ and R$^3$=CH$_3$)

The titled compound was prepared in the same manner as described in Preparative Example 33 by using 1-butyl-5-isopropyl-6-(methylthio)uracil in place of 1-butyl-5-ethyl-6-(methylthio)uracil.

Yield: 88%; IR (KBr): 1154 (SO$_2$), 1676, 1696 (CO) cm$^{-1}$; $^1$H NMR (CDCl$_3$/TMS): δ 0.95 (t, J=7.4 Hz, 3 H, NCH$_2$CH$_2$CH$_2$CH$_3$), 1.34 (m, 2 H, NCH$_2$CH$_2$CH$_2$), 1.38 (d, J=6.9 Hz, 6 H, CH(CH$_3$)$_2$), 1.73 (m, 2 H, NCH$_2$CH$_2$), 3.26 (s, 3 H, SO$_2$CH$_3$), 3.76 (septet, J=6.9 Hz, 1 H, CH(CN)$_2$), 4.21 (t, J=7.8 Hz, 2 H, NCH$_2$), 8.92 (br s, 1 H, NH); $^{13}$C NMR (CDCl$_3$): δ 13.63, 19.90, 20.00, 28.92, 31.72, 45.99, 48.06, 127.52, 149.18, 150.36, 160.86

Preparative Example 36

Preparation of 5-isopropyl-6-(methylsulfonyl)-1-(3-phenylpropyl)uracil (a compound of the general formula (XIII) wherein R$^1$=CH(CH$_3$)$_2$ and R$^3$=Ph)

The titled compound was prepared in the same manner as described in Preparative Example 33 by using 5-isopropyl-6-(methylthio)-1-(3-phenylpropyl)uracil in place of 1-butyl-5-ethyl-6-(methylthio)uracil.

Yield: 95%; IR (KBr): 1154 (SO$_2$), 1688 (CO) cm$^{-1}$; $^1$H NMR (CDCl$_3$/TMS): δ 1.37 (d, J=6.9 Hz, 6 H, CH(CH$_3$)$_2$), 2.11 (quintet, J=7.7 Hz, 2 H, NCH$_2$CH$_2$), 2.67 (t, J=7.7 Hz, 2 H, CH$_2$Ph), 3.13 (s, 3 H, SO$_2$CH$_3$), 3.72 (septet, J=6.9 Hz, 1 H, CH(CH$_3$)$_2$), 4.22 (t, J=7.7 Hz, 2 H, NCH$_2$), 7.14–7.33 (m, 5 H, Ar H), 8.85 (br s, 1 H, NH); $^{13}$C NMR (CDCl$_3$): δ 20.01, 28.99, 30.94, 32.92, 45.76, 48.03, 126.12, 127.75, 128.38, 128.45, 140.68, 149.09, 150.30, 160.76

Preparative Example 37

Preparation of 1-(4-acetoxybutyl)-5,6-dihydro-6-(dimethylthio)-5-ethyl-2-thiouracil (a compound of the general formula (XIV) wherein R$^1$=C$_2$H$_5$ and R$^3$=CH$_2$OAc)

A suspension of N-[3,3-(dimethylthio)-2-ethylacryloyl]-N'-(4-hydroxybutyl) thiourea (4.50 g, 14.0 mmol) and methanesulfonic acid (1.35 g, 14.0 mmol) in AcOH (50 mL) was stirred at room temperature for 1.5 h. The reaction mixture was evaporated to dryness and the residue was dissolved in CH$_2$Cl$_2$ (150 mL). The CH$_2$Cl$_2$ solution was washed with saturated NaHCO$_3$ solution (50 mL) and brine (50 mL), dried over anhydrous MgSO$_4$, filtered, and evaporated to dryness. The residue was purified by flash column chromatography on silica gel with EtOAc-hexane (4:1) as eluent to give 4.50 g of the titled compound as an oil.

Yield: 88%; IR (neat): 1648 (CO),1737 ($CO_2$) cm$^{-1}$; $^1$H NMR (CDCl$_3$/TMS): δ 1.03 (t, J=7.4 Hz, 3 H, CH$_2$CH$_3$), 1.63–1.84 (m, 5 H, NCH$_2$CH$_2$CH$_2$ and 1 H of CH$_2$CH$_3$), 1.97–2.13 (m, 1 H, CH$_2$CH$_3$), 2.04 (s, 3 H, COCH$_3$), 2.16 (s, 3 H, SCH$_3$), 2.25 (s, 3 H, SCH$_3$), 2.75 (dd, J=10.8 Hz, J=3.6 Hz, 1 H, H-5), 3.40 (br s, 2 H, NCH$_2$), 4.08 (t, J=5.4 Hz, 2 H, CH$_2$OAc); $^{13}$C NMR(CDCl$_3$): δ 12.38, 12.61, 13.96, 20.90, 21.02, 25.94, 29.61, 43.97, 52.36, 63.94, 69.70, 163.17, 170.99, 175.51

Preparative Example 38

Preparation of 1-butyl-5,6-dihydro-6-(dimethylthio)-5-ethyl-2-thiouracil (a compound of the general formula (XIV) wherein $R^1$=C$_2$H$_5$ and $R^3$=CH$_3$)

The titled compound was prepared in the same manner as described in Preparative Example 37 by using N-butyl-N'-[3,3-(dimethylthio)-2-ethylacryloyl]thiourea in place of N-[3,3-(dimethylthio)-2-ethylacryloyl]-N'-(4-hydroxybutyl)thiourea.

Yield: 99%; IR (KBr): 1652 (CO) cm$^{-1}$; $^1$H NMR (CDCl$_3$/TMS): δ 0.93 (t, J=7.4 Hz, 3 H, NCH$_2$CH$_2$CH$_2$CH$_3$), 1.04 (t, J=7.5 Hz, 3 H, CH$_2$CH$_3$), 1.37 (m, 2 H, NCH$_2$CH$_2$CH$_2$), 1.60 (m, 2 H, NCH$_2$CH$_2$), 1.74 (m, 1 H, CH$_2$CH$_3$), 2.03 (m, 1 H, CH$_2$CH$_3$), 2.16 (s, 3 H, SCH$_3$), 2.25 (s, 3 H, SCH$_3$), 2.77 (dd, J=10.8 Hz, J=3.6 Hz, 1 H, H-5), 3.33 (m, 2 H, NCH$_2$), 9.08 (br s, 1 H, NH); $^{13}$C NMR (CDCl$_3$): δ 12.40, 12.63, 13.75, 13.99, 20.05, 21.06, 31.84, 44.16, 52.35, 69.75, 163.39, 175.74

Preparative Example 39

Preparation of 1-(4-acetoxybutyl)-5,6-dihydro-6-(dimethylthio)-5-isopropyl-2-thiouracil (a compound of the general formula (XIV) wherein $R^1$=CH(CH$_3$)$_2$ and $R^3$CH$_2$OAc)

The titled compound was prepared in the same manner as described in Preparative Example 37 by using N-[3,3-(dimethylthio)-2-isopropylacryloyl]-N'-(4-hydroxybutyl)thiourea in place of N-[3,3-(dimethylthio)-2-ethylacryloyl]-N'-(4-hydroxybutyl)thiourea.

Yield: 94%; IR (KBr): 1644 (CO), 1742 ($CO_2$) cm$^{-1}$; $^1$H NMR (CDCl$_3$/TMS): δ 1.04 (d, J=6.6 Hz, 3 H, CHCH$_3$), 1.19 (d, J=6.6 Hz, 3 H, CHCH$_3$), 1.69 (m, 4 H, NCH$_2$CH$_2$CH$_2$), 2.05 (s, 3 H, COCH$_3$), 2.13 (s, 3 H, SCH$_3$), 2.25 (s, 3 H, SCH$_3$), 2.46 (m, 1 H, CH(CH$_3$)$_2$), 2.82 (d, J=2.7 Hz, 1 H, H-5), 3.36 (br s, 2 H, NCH$_2$), 4.08 (br s, 2 H, CH$_2$OAc); $^{13}$C NMR (CDCl$_3$): δ 12.79, 14.33, 20.14, 20.98, 25.01, 26.08, 26.67, 28.31, 45.98, 56.89, 64.10, 69.43, 156.74, 171.09, 172.39

Preparative Example 40

Preparation of 1-butyl-5,6-dihydro-6-(dimethylthio)-5-isopropyl-2-thiouracil (a compound of the general formula (XIV) wherein $R^1$=CH(CH$_3$)$_2$ and $R^3$=CH$_3$)

The titled compound was prepared in the same manner as described in Preparative Example 37 by using N-butyl-N'-[3,3-(dimethylthio)-2-isopropylacryloyl]thiourea in place of N-[3,3-(dimethylthio)-2-ethylacryloyl]-N'-(4-hydroxybutyl)thiourea.

Yield: 99%; IR (KBr): 1633 (CO) cm$^{-1}$; $^1$H NMR (CDCl$_3$/TMS): δ 0.92 (t, J=7.2 Hz, 3 H, NCH$_2$CH$_2$CH$_2$CH$_3$), 1.02 (d, J =6.6 Hz, 3 H, CHCH$_3$), 1.18 (d, J=6.6 Hz, 3 H, CHCH$_3$), 1.37 (m, 2 H, NCH$_2$CH$_2$CH$_2$), 1.60 (m, 2 H, NCH$_2$CH$_2$), 2.13 (s, 3 H, SCH$_3$), 2.25 (s, 3 H, SCH$_3$), 2.44 (m, 1 H, CH(CH$_3$)$_2$), 2.78 (d, J=3.3 Hz, 1 H, H-5), 3.36 (br s, 2 H, NCH$_2$), 9.62 (br s, 1 H, NH); $^{13}$C NMR (CDCl$_3$): δ 12.64, 13.77, 14.21, 20.05, 20.17, 24.96, 28.11, 31.96, 44.63, 56.15, 69.84, 162.12, 174.35

Preparative Example 41

Preparation of 1-(4-acetoxybutyl)-5-ethyl-6-(methylsulfinyl)-2-thiouracil (a compound of the general formula (XV) wherein $R^1$=C$_2$H$_5$ and $R^3$=CH$_2$OAc)

To a stirred solution of 1-(4-acetoxybutyl)-5,6-dihydro-6-(dimethylthio)-5-ethyl-2-thiouracil (1.46 g, 4.0 mmol) in MeOH (50 mL) was added a solution of NaIO$_4$ (5.14 g, 24.0 mmol) in H$_2$O (50 mL) at room temperature. The mixture was heated under reflux for 1.5 h and filtered. The filtrate was concentrated to 50 mL in volume. The concentrate was extracted by using continuous extractor with CHCl$_3$. The CHCl$_3$ solution was dried over anhydrous MgSO$_4$, filtered, and evaporated to dryness. The residue was purified by flash column chromatography on silica gel with MeOH-CHCl$_3$ (3:97) as eluent to give 0.77 g of the titled compound.

Yield: 70%; IR (KBr): 1054 (SO), 1630 (CO), 1734 ($CO_2$) cm$^{-1}$; $^1$H NMR (CDCl$_3$/TMS): δ 1.15 (t, J=7.4 Hz, 3 H, CH$_2$CH$_3$), 1.73 (br S, 4 H, NCH$_2$CH$_2$CH$_2$), 2.06 (s, 3 H, COCH$_3$), 2.64 (m, 2 H, CH$_2$CH$_3$), 2.86 (s, 3 H, SOCH$_3$), 3.58 (br s, 2 H, NCH$_2$), 4.10 (t, J=5.7 Hz, 2 H, CH$_2$OAc), 6.94(br s, 1 H, NH)

Preparative Example 42

Preparation of 1-butyl-5-ethyl-6-(methylsulfinyl)-2-thiouracil (a compound of the general formula (XV) wherein $R^1$=C$_2$H$_5$ and $R^3$=CH$_3$)

The titled compound was prepared in the same manner as described in Preparative Example 41 by using 1-butyl-5,6-dihydro-6-(dimethylthio)-5-ethyl-2-thiouracil in place of 1-(4-acetoxybutyl)-5,6-dihydro-6-(dimethylthio)-5-ethyl-2-thiouracil.

Yield: 73%; IR (KBr): 1042 (SO), 1633 (CO) cm$^{-1}$; $^1$H NMR (CDCl$_3$/TMS): δ 0.95 (t, J=7.4 Hz, 3 H, NCH$_2$CH$_2$CH$_2$CH$_3$), 1.15 (t, J=7.5 Hz, 3 H, CH$_2$CH$_3$), 1.42 (m, 2 H, NCH$_2$CH$_2$CH$_2$), 1.65 (m, 2 H, NCH$_2$CH$_2$), 2.65 (m, 2 H, CH$_2$CH$_3$), 2.85 (s, 3 H, SOCH$_3$), 3.52 (br s, 2 H, NCH$_2$), 6.63 (br s, 1 H, NH)

Preparative Example 43

Preparation of 1-(4-acetoxybutyl)-5-isopropyl-6-(methylsulfinyl)-2-thiouracil (a compound of the general formula (XV) wherein $R^1$=CH(CH$_3$)$_2$ and $R^3$=CH$_2$OAc)

The titled compound was prepared in the same manner as described in Preparative Example 41 by using 1-(4-acetoxybutyl)-5,6-dihydro-6-(dimethylthio)-5-isopropyl-2-thiouracil in place of 1-(4-acetoxybutyl)-5,6-dihydro-6-(dimethylthio)-5-ethyl-2-thiouracil.

Yield: 57%; IR (KBr): 1060 (SO), 1622 (CO), 1737 ($CO_2$) cm$^{-1}$; $^1$H NMR (CDCl$_3$/TMS): δ 1.36 (d, J=7.5 Hz, 3 H, CHCH$_3$), 1.38 (d, J=7.2 Hz, 3 H, CHCH$_3$), 1.73 (br s, 4 H, NCH$_2$CH$_2$CH$_2$), 2.05 (s, 3 H, COCH$_3$), 2.83 (s, 3 H, SOCH$_3$), 2.90 (septet, J=6.6 Hz, 1 H, CH(CH$_3$)$_2$), 3.56 (br s, 2 H, NCH$_2$), 4.10 (t, J=5.9 Hz, 2 H, CH$_2$OAc), 6.81 (br s, 1 H, NH); $^{13}$C NMR (CDCl$_3$): δ 19.91, 20.66, 20.97, 25.59, 26.00, 32.96, 41.99, 42.46, 63.83, 136.05, 149.97, 152.43, 171.06

Preparative Example 44

Preparation of 1-butyl-5-isopropyl-6-(methylsulfinyl)-2-thiouracil (a compound of the general formula (XV) wherein $R^1$=CH(CH$_3$)$_2$ and $R^3$=CH$_3$)

The titled compound was prepared in the same manner as described in Preparative Example 41 by using 1-butyl-5,6-dihydro-6-(dimethylthio)-5-isopropyl-2-thiouracil in place of 1-(4-acetoxybutyl)-5,6-dihydro-6-(dimethylthio)-5-ethyl-2-thiouracil.

Yield: 63%; IR (KBr): 1052 (SO), 1643 (CO) cm$^{-1}$; $^1$H NMR (CDCl$_3$/TMS): δ 0.94 (t, J=7.2 Hz, 3 H, NCH$_2$CH$_2$CH$_2$CH$_3$), 1.36 (d, J =7.8 Hz, 3 H, CHCH$_3$), 1.39 (d, J=7.2 Hz, 3 H, CHCH$_3$), 1.41 (m, 2 H, NCH$_2$CH$_2$CH$_2$), 1.64 (m, 2 H, NCH$_2$CH$_2$), 2.83 (s, 3 H, SOCH$_3$), 2.90 (septet, J=6.9 Hz, 1 H, CH(CH$_3$)$_2$), 3.50 (br s, 2 H, NCH$_2$), 6.57 (br s, 1 H, NH); $^{13}$C NMR (CDCl$_3$): δ 13.69, 19.92, 20.00, 20.67, 31.01, 32.94, 41.98, 42.71, 102.17, 136.14, 149.86, 152.42

Example 1

Preparation of 5-ethyl-1-[(2-hydroxyethoxy)methyl]-6-(phenylselenenyl)-2-thiouracil (Compound No. 1)

To a stirred solution of 1-[[2-(tert-butyldimethylsiloxy) ethoxy]methyl]-5-ethyl-2-thiouracil (0.20 g, 0.58 mmol) in anhydrous THF (4 mL) was added LDA (0.97 mL of 1.5M solution in cyclohexane, 1.45 mmol) dropwise under a nitrogen atmosphere, at a rate such that the temperature did not exceed −70° C. After the mixture was stirred for 1 h, diphenyl diselenide (0.27 g, 0.87 mmol) dissolved in anhydrous THF (2 mL) was added dropwise. The mixture was stirred for 1 h below −70° C. and allowed to warm to room temperature. The solution was acidified with concentrated HCl to pH 1.2 and stirred at room temperature for 2 h. The reaction mixture was poured into saturated NaHCO$_3$ solution (15 mL) and it was then extracted with EtOAc (3×15 mL). The organic phase was washed with brine (15 mL), dried over anhydrous MgSO$_4$, and concentrated to dryness. The residue was purified by flash column chromatography on silica gel with EtOAc-hexane (1:1) as eluent to give 0.19 g (85%) of the target compound.

IR (KBr): 3398, 1680, 1666 cm$^{-1}$; $^1$H NMR (CDCl$_3$/TMS): δ 0.92 (t, J=7.4 Hz, 3 H, CH$_2$CH$_3$), 1.95 (br s, 1 H, OH), 2.68 (q, J=7.4 Hz, 2 H, CH$_2$CH$_3$), 3.60–3.80 (m, 4 H, OCH$_2$CH$_2$O), 6.20 (br s, 2 H, NCH$_2$O), 7.25–7.40 (m, 5 H, Ar H), 9.83 (br s, 1 H, NH)

Example 2

Preparation of 5-ethyl-1-[(2-hydroxyethoxy)methyl]-6-[(3-methylphenyl)selenenyl]-2-thiouracil (Compound No. 2)

The titled compound was prepared in the same manner as described in Example 1 by using bis(3-methylphenyl) diselenide in place of diphenyl diselenide.

Yield: 77%; IR (KBr): 3396, 1668 cm$^{-1}$; $^1$H NMR (CDCl$_3$/TMS): δ 0.92 (t, J=7.4 Hz, 3 H, CH$_2$CH$_3$), 1.93 (br s, 1 H, OH), 2.34 (s, 3 H, CH$_3$), 2.68 (q, J=7.4 Hz, 2 H, CH$_2$CH$_3$), 3.68–3.75 (m, 4 H, OCH$_2$CH$_2$O), 6.20 (br s, 2 H, NCH$_2$O), 7.11–7.24 (m, 4 H, Ar H), 9.62 (br s, 1 H, NH)

Example 3

Preparation of 6-[(3,5-dimethylphenyl)selenenyl]-5-ethyl-1-[(2-hydroxyethoxy) methyl]-2-thiouracil (Compound No. 3)

The titled compound was prepared in the same manner as described in Example 1 by using bis(3,5-dimethylphenyl) diselenide in place of diphenyl diselenide.

Yield: 62%; IR (KBr): 3480, 1674 cm$^{-1}$; $^1$H NMR (CDCl$_3$/TMS): δ 0.93 (t, J=7.4 Hz, 3 H, CH$_2$CH$_3$), 2.07 (br s, 1 H, OH), 2.29 (s, 6 H, 2 CH$_3$), 2.68 (q, J=7.4 Hz, 2 H, CH$_2$CH$_3$), 3.65–3.80 (m, 4 H, OCH$_2$CH$_2$O), 6.20 (br s, 2 H, NCH$_2$O), 6.93 (s, 1 H, Ar H), 6.97 (s, 2 H, Ar H), 10.08 (br s, 1 H, NH)

Example 4

Preparation of 1-[(2-hydroxyethoxy)methyl]-5-isopropyl-6-(phenylselenenyl)-2-thiouracil (Compound No. 4)

The titled compound was prepared in the same manner as described in Example 1 by using 1-[[2-(tert-butyldimethylsiloxy)ethoxy]methyl]-5-isopropyl-2-thiouracil in place of 1-[[2-(tert-butyldimethylsiloxy) ethoxy]methyl]-5-ethyl-2-thiouracil.

Yield: 62%; IR (KBr): 3398, 1664cm$^{-1}$; $^1$H NMR (CDCl$_3$/TMS): δ 1.05 (d, J=6.9 Hz, 6 H, CH(CH$_3$)$_2$), 1.95 (br s, 1 H, OH), 3.39 (septet, J=6.9 Hz, 1 H, CH(CH$_3$)$_2$), 3.65–3.80 (m, 4 H, OCH$_2$CH$_2$O), 6.29 (br s, 2 H, NCH$_2$O), 7.27–7.45 (m, 5 H, Ar H), 9.63 (br s, 1 H, NH)

Example 5

Preparation of 1-[(2-hydroxyethoxy)methyl]-5-isopropyl-6-[(3-methylphenyl)-selenenyl]-2-thiouracil (Compound No. 5)

The titled compound was prepared in the same manner as described in Example 1 by using 1-[[2-(tert-butyldimethylsiloxy)ethoxy]methyl]-5-isopropyl-2-thiouracil and bis(3-methylphenyl) diselenide in place of 1-[[2-(tert-butyldimethylsiloxy)ethoxy]methyl]-5-ethyl-2-thiouracil and diphenyl diselenide, respectively.

Yield: 59%; IR (KBr): 3391, 1664 cm$^{-1}$; $^1$H NMR (CDCl$_3$/TMS): δ 1.06 (d, J=6.9 Hz, 6 H, CH(CH$_3$)$_2$), 1.93 (br s, 1 H, OH), 2.34 (s, 3 H, CH$_3$), 3.39 (septet, J=6.9 Hz, 1 H, CH(CH$_3$)$_2$), 3.68–3.82 (m, 4 H, OCH$_2$CH$_2$O), 6.29 (br s, 2 H, NCH$_2$O), 7.11–7.24 (m, 4 H, Ar H), 9.54 (br s, 1 H, NH)

Example 6

Preparation of 6-[(3,5-dimethylphenyl)selenenyl]-1-[(2-hydroxyethoxy)methyl]-5-isopropyl-2-thiouracil (Compound No. 6)

The titled compound was prepared in the same manner as described in Example 1 by using 1-[[2-(tert-butyldimethylsiloxy)ethoxy]methyl]-5-isopropyl-2-thiouracil and bis(3,5-dimethylphenyl) diselenide in place of 1-[[2-(tert-butyldimethylsiloxy)ethoxy]methyl]-5-ethyl-2-thiouracil and diphenyl diselenide, respectively.

Yield: 67%; IR (KBr): 3547, 1652 cm$^{-1}$; $^1$H NMR (CDCl$_3$/TMS): δ 1.07 (d, .=6.9 Hz, 6 H, CH(CH$_3$)$_2$), 2.08 (br s, 1 H, OH), 2.29 (s, 6 H, 2 CH$_3$), 3.39 (septet, J=6.9 Hz, 1 H, CH(CH$_3$)$_2$), 3.70–3.80 (m, 4 H, OCH$_2$CH$_2$O), 6.29 (br s, 2 H, NCH$_2$O), 6.93 (s, 1 H, Ar H), 7.00 (s, 2 H, Ar H), 9.97 (br s, 1 H, NH)

Example 7

Preparation of 5-ethyl-1-[(2-hydroxyethoxy)methyl]-6-(phenylselenenyl)uracil (Compound No. 7)

To a stirred solution of 1-[[2-(tert-butyldimethylsiloxy) ethoxy]methyl]-5-ethyluracil (0.20 g, 0.61 mmol) in anhydrous THF (4 mL) was added lithium bis(trimethylsilyl) amide (1.52 mL of 1.0M solution in THF, 1.52 mmol) dropwise under a nitrogen atmosphere, at a rate such that the temperature did not exceed −70° C. After the mixture was stirred for 1 h, diphenyl diselenide (0.29 g, 0.91 mmol) dissolved in anhydrous THF (2 mL) was added dropwise. The mixture was stirred for 1 h below −70° C. and then at room temperature for 16 h. The solution was acidified with concentrated HCl to pH 1.2 and stirred at room temperature for 2 h. The reaction mixture was poured into saturated NaHCO$_3$ solution (15 mL) and it was then extracted with EtOAc (3×15 mL). The organic phase was washed with brine (15 mL), dried over anhydrous MgSO$_4$, and concentated to dryness. The residue was purified by flash column chromatography on silica gel with EtOAc-hexane (3:1) as eluent to give 0.18 g (80%) of the target compound.

IR (KBr): 3410, 1708, 1665 cm$^{-1}$; $^1$H NMR (CDCl$_3$/ TMS): δ 0.97 (t, J=7.5 Hz, 3 H, CH$_2$CH$_3$), 2.06 (br s, 1 H, OH), 2.71 (q, J=7.5 Hz, 2 H, CH$_2$CH$_3$), 3.63 (s, 4 H, OCH$_2$CH$_2$O), 5.61 (s, 2 H, NCH$_2$O), 7.28–7.40 (m, 5 H, Ar H), 9.11 (br s, 1 H, NH)

Example 8

Preparation of 5-ethyl-1-[(2-hydroxyethoxy)methyl]-6-[(3-methylphenyl)-selenenyl]uracil (Compound No. 8)

The titled compound was prepared in the same manner as described in Example 7 by using bis(3-methylphenyl) diselenide in place of diphenyl diselenide.

Yield: 78%; IR (KBr): 3482, 1670 cm$^{-1}$; $^1$H NMR (CDCl$_3$/TMS): δ 0.97 (t, J=7.4 Hz, 3 H, CH$_2$CH$_3$), 2.06 (br s, 1 H, OH), 2.33 (s, 3 H, CH$_3$), 2.71 (q, J=7.4 Hz, 2 H, CH$_2$CH$_3$), 3.64 (s, 4 H, OCH$_2$CH$_2$O), 5.61 (s, 2 H, NCH$_2$O), 7.08–7.22 (m, 4 H, Ar H), 9.09 (br s, 1 H, NH)

Example 9

Preparation of 6-[(3,5-dimethylphenyl)selenenyl]-5-ethyl-1-[(2-hydroxyethoxy)-methyl]uracil (Compound No. 9)

The titled compound was prepared in the same manner as described in Example 7 by using bis(3,5-dimethylphenyl) diselenide in place of diphenyl diselenide.

Yield: 73%; IR (KBr): 3408, 1707, 1673 cm$^{-1}$; $^1$H NMR (CDCl$_3$/TMS): δ 0.97 (t, J=7.4 Hz, 3 H, CH$_2$CH$_3$), 2.23 (br s, 1 H, OH), 2.28 (s, 6 H, 2 CH$_3$), 2.71 (q, J=7.4 Hz, 2 H, CH$_2$CH$_3$), 3.66 (s, 4 H, OCH$_2$CH$_2$O), 5.61 (s, 2 H, NCH$_2$O), 6.91 (s, 1 H, Ar H), 6.95 (s, 2 H, Ar H), 9.58 (br s, 1 H, NH)

Example 10

Preparation of 1-[(2-hydroxyethoxy)methyl]-5-isopropyl-6-(phenylselenenyl)-uracil (Compound No. 10)

The titled compound was prepared in the same manner as described in Example 7 by using 1-[[2-(tert-butyldimethylsiloxy)ethoxy]methyl]-5-isopropyluracil in place of 1-[[2-(tert-butyldimethylsiloxy)ethoxy]methyl]-5-ethyluracil.

Yield: 64%; IR (KBr): 3394, 1674 cm$^{-1}$; $^1$H NMR (CDCl$_3$/TMS): δ 1.12 (d, J=6.9 Hz, 6 H, CH(CH$_3$)$_2$), 2.00 (br s, 1 H, OH), 3.46 (septet, J=6.9 Hz, 1 H, CH(CH$_3$)$_2$), 3.66 (s, 4 H, OCH$_2$CH$_2$O), 5.69 (s, 2 H, NCH$_2$O), 7.27–7.41 (m, 5 H, Ar H), 8.82 (br s, 1 H, NH)

Example 11

Preparation of 1-[(2-hydroxyethoxy)methyl]-5-isopropyl-6-[(3-methylphenyl)-selenenyl]uracil (Compound No. 11)

The titled compound was prepared in the same manner as described in Example 7 by using 1-[[2-(tert-butyldimethylsiloxy)ethoxy]methyl]-5-isopropyluracil and bis(3-methylphenyl) diselenide in place of 1-[[2-(tert-butyldimethylsiloxy)ethoxy]methyl]-5-ethyluracil and diphenyl diselenide.

Yield: 68%; IR (KBr): 3371, 1673 cm$^{-1}$; $^1$H NMR (CDCl$_3$/TMS): δ 1.13 (d, J=6.9 Hz, 6 H, CH(CH$_3$)$_2$), 1.93 (br s, 1 H, OH), 2.33 (s, 3 H, CH$_3$), 3.46 (septet, J=6.9 Hz, 1 H, CH(CH$_3$)$_2$), 3.67 (s, 4 H, OCH$_2$CH$_2$O), 5.68 (s, 2 H, NCH$_2$O), 7.09–7.20 (m, 4 H, Ar H), 8.56 (br s, 1 H, NH)

Example 12

Preparation of 6-[(3,5-dimethylphenyl)selenenyl]-1-[(2-hydroxyethoxy)methyl]-5-isopropyluracil (Compound No. 12)

The titled compound was prepared in the same manner as described in Example 7 by using 1-[[2-(tert-butyldimethylsiloxy)ethoxy]methyl]-5-isopropyluracil and bis(3,5-dimethylphenyl) diselenide in place of 1-[[2-(tert-butyldimethylsiloxy)ethoxy]methyl]-5-ethyluracil and diphenyl diselenide.

Yield: 45%; IR (KBr): 3420, 1709, 1667 cm$^{-1}$; $^1$H NMR (CDCl$_3$/TMS): δ 1.14 (d, J=6.9 Hz, 6 H, CH(CH$_3$)$_2$), 2.21 (br s, 1 H, OH), 2.28 (s, 6 H, 2 CH$_3$), 3.46 (septet, J=6.9 Hz, 1 H, CH(CH$_3$)$_2$), 3.68 (s, 4 H, OCH$_2$CH$_2$O), 5.69 (s, 2 H, NCH$_2$O), 6.91 (s, 1 H, Ar H), 6.98 (s, 2 H, Ar H), 9.37 (br s, 1 H, NH)

Example 13

Preparation of 1-(ethoxymethyl)-5-ethyl-6-(phenylselenenyl)-2-thiouracil (Compound No. 15)

To a stirred solution of 1-(ethoxymethyl)-5-ethyl-2-thiouracil (0.20 g, 0.93 mmol) in anhydrous THF (6 mL) was added LDA (1.56 mL of 1.5M solution in cyclohexane, 2.33 mmol) dropwise under a nitrogen atmosphere, at a rate such that the temperature did not exceed −70° C. After the mixture was stirred for 1 h, diphenyl diselenide (0.44 g, 1.41 mmol) dissolved in anhydrous THF (3 mL) was added dropwise. The mixture was stirred for 1 h below −70° C. The reaction mixture was quenched with AcOH (0.27 mL, 4.66 mmol), and then allowed to warm to room temperature. The suspension was partitioned between EtOAc (25 mL) and H$_2$O (25 mL). The aqueous phase was extracted with EtOAc (2×25 mL). The combined organic phase was washed with saturared NaHCO$_3$ solution (25 mL) and brine (25 mL), dried over anhydrous MgSO$_4$, and evaporated to dryness. The residue was purified by flash column chromatography on silica gel with EtOAc-hexane (1:4) as eluent to give 0.23 g (89%) of the target compound.

IR (KBr): 1644 cm$^{-1}$; $^1$H NMR (CDCl$_3$/TMS): δ 0.86 (t, J=7.4 Hz, 3 H, CH$_2$CH$_3$), 1.17 (t, J=7.1 Hz, 3 H, OCH$_2$CH$_3$), 2.63 (q, J=7.4 Hz, 2 H, CH$_2$CH$_3$), 3.67 (q, J=7.1 Hz, 2 H, OCH$_2$CH$_3$), 6.20 (br s, 2 H, NCH$_2$O), 7.30–7.40 (m, 5 H, Ar H), 9.66 (br s, 1 H, NH)

Example 14

Preparation of 1-(ethoxymethyl)-5-ethyl-6-[(3-methylphenyl)selenenyl]-2-thiouracil (Compound No. 16)

The titled compound was prepared in the same manner as described in Example 13 by using bis(3-methylphenyl) diselenide in place of diphenyl diselenide.

Yield: 63%; IR (KBr): 1673 cm$^{-1}$; $^1$H NMR (CDCl$_3$/TMS): δ 0.86 (t, J=7.4 Hz, 3 H, CH$_2$CH$_3$), 1.18 (t, J=7.1 Hz, 3 H, OCH$_2$CH$_3$), 2.33 (s, 3 H, CH$_3$), 2.63 (q, J=7.4 Hz, 2 H, CH$_2$CH$_3$), 3.67 (q, J=7.1 Hz, 2 H, OCH$_2$CH$_3$), 6.19 (br s, 2 H, NCH$_2$O), 7.08–7.23 (m, 4 H, Ar H), 9.58 (br s, 1 H, NH)

Example 15

Preparation of 6-[(3,5-dimethylphenyl)selenenyl]-1-(ethoxymethyl)-5-ethyl-2-thiouracil (Compound No. 17)

The titled compound was prepared in the same manner as described in Example 13 by using bis(3,5-dimethylphenyl) diselenide in place of diphenyl diselenide.

Yield: 74%; IR (KBr): 1650 cm$^{-1}$; $^1$H NMR (CDCl$_3$/TMS): δ 0.87 (t, J=7.4 Hz, 3 H, CH$_2$CH$_3$), 1.19 (t, J=6.9 Hz, 3 H, OCH$_2$CH$_3$), 2.28 (s, 6 H, 2 CH$_3$), 2.64 (q, J=7.4 Hz, 2 H, CH$_2$CH$_3$), 3.68 (q, J=6.9 Hz, 2 H, OCH$_2$CH$_3$), 6.20 (br s, 2 H, NCH$_2$O), 6.92 (s, 1 H, Ar H), 6.98 (s, 2 H, Ar H), 10.03 (br s, 1 H, NH)

Example 16

Preparation of 6-[(3,5-difluorophenyl)selenenyl]-1-(ethoxymethyl)-5-ethyl-2-thiouracil (Compound No. 18)

The titled compound was prepared in the same manner as described in Example 13 by using bis(3,5-difluorophenyl) diselenide in place of diphenyl diselenide.

Yield: 26%; IR (KBr): 1644 cm$^{-1}$; $^1$H NMR (CDCl$_3$/TMS): δ 0.95 (t, J=7.4 Hz, 3 H, CH$_2$CH$_3$), 1.16 (t, J=6.9 Hz, 3 H, OCH$_2$CH$_3$), 2.62 (q, J=7.4 Hz, 2 H, CH$_2$CH$_3$), 3.67 (q, J=6.9 Hz, 2 H, OCH$_2$CH$_3$), 6.16 (br s, 2 H, NCH$_2$O), 6.89 (m, 2 H, Ar H), 6.75 (m, 1 H, Ar H), 9.60 (br s, 1 H, NH)

Example 17

Preparation of 1-[(benzyloxy)methyl]-5-ethyl-6-(phenylselenenyl)-2-thiouracil (Compound No. 19)

The titled compound was prepared in the same manner as described in Example 13 by using 1-[(benzyloxy)methyl]-5-ethyl-2-thiouracil in place of 1-(ethoxymethyl)-5-ethyl-2-thiouracil.

Yield: 38%; IR (KBr): 3448, 1672 cm$^{-1}$; $^1$H NMR (CDCl$_3$/TMS): δ 0.82 (t, J=7.4 Hz, 3 H, CH$_2$CH$_3$), 2.57 (q, J=7.4 Hz, 2 H, CH$_2$CH$_3$), 4.73 (s, 2 H, CH$_2$Ph), 6.28 (br s, 2 H, NCH$_2$O), 7.23–7.38 (m, 10 H, Ar H), 9.46 (br s, 1 H, NH)

Example 18

Preparation of 1-[(benzyloxy)methyl]-5-ethyl-6-[(3-methylphenyl)selenenyl]-2-thiouracil (Compound No. 20)

The titled compound was prepared in the same manner as described in Example 13 by using 1-[(benzyloxy)methyl]-5-ethyl-2-thiouracil and bis(3-methylphenyl) diselenide in place of 1-(ethoxymethyl)-5-ethyl-2-thiouracil and diphenyl diselenide, respectively.

Yield: 31%; IR (KBr): 1641 cm$^{-1}$; $^1$H NMR (CDCl$_3$/TMS): δ 0.83 (t, J=7.4 Hz, 3 H, CH$_2$CH$_3$), 2.29 (s, 3 H, CH$_3$), 2.58 (q, J=7.4 Hz, 2 H, CH$_2$CH$_3$), 4.73 (s, 2 H, CH$_2$Ph), 6.28 (br s, 2 H, NCH$_2$O), 7.04–7.38 (m, 9 H, Ar H), 9.51 (br s, 1 H, NH)

Example 19

Preparation of 1-[(benzyloxy)methyl]-6-[(3,5-dimethylphenyl)selenenyl]-5-ethyl-2-thiouracil (Compound No. 21)

The titled compound was prepared in the same manner as described in Example 13 by using 1-[(benzyloxy)methyl]-5-ethyl-2-thiouracil and bis(3,5-dimethylphenyl) diselenide in place of 1-(ethoxymethyl)-5-ethyl-2-thiouracil and diphenyl diselenide, respectively.

Yield: 43%; IR (KBr): 1700 cm$^{-1}$; $^1$H NMR (CDCl$_3$/TMS): δ 0.84 (t, J=7.4 Hz, 3 H, CH$_2$CH$_3$), 2.25 (s, 6 H, 2 CH$_3$), 2.59 (q, J=7.4 Hz, 2 H, CH$_2$CH$_3$), 4.73 (s, 2 H, CH$_2$Ph), 6.27 (br s, 2 H, NCH$_2$O), 6.90 (s, 1 H, Ar H), 6.93 (s, 2 H, Ar H), 7.25–7.33 (m, 5 H, Ar H), 9.48 (br s, 1 H, NH)

Example 20

Preparation of 1-(ethoxymethyl)-5-isopropyl-6-(phenylselenenyl)-2-thiouracil (Compound No. 22)

The titled compound was prepared in the same manner as described in Example 13 by using 1-(ethoxymethyl)-5-isopropyl-2-thiouracil in place of I-(ethoxymethyl)-5-ethyl-2-thiouracil.

Yield: 82%; IR (KBr): 1651 cm$^{-1}$; $^1$H NMR (CDCl$_3$/TMS): δ 0.99 (d, J=6.9 Hz, 6 H, CH(CH$_3$)$_2$), 1.20 (t, J=7.1 H 3 H, OCH$_2$CH$_3$), 3.35 (septet, J=6.9 Hz, 1 H, CH(CH$_3$)$_2$), 3.68 (q, J=7.1 Hz, 2 H, OCH$_2$CH$_3$), 6.27 (br s, 2 H, NCH$_2$O), 7.30–7.43 (m, 5 H, Ar H), 9.48 (br s, 1 H, NH)

Example 21

Preparation of 1-(ethoxymethyl)-5-isopropyl-6-[(3-methylphenyl)selenenyl]-2-thiouracil (Compound No. 23)

The titled compound was prepared in the same manner as described in Example 13 by using 1-(ethoxymethyl)-5-isopropyl-2-thiouracil and bis(3-methylphenyl) diselenide in place of 1-(ethoxymethyl)-5-ethyl-2-thiouracil and diphenyl diselenide, respectively.

Yield: 73%; IR (KBr): 1646 cm$^{-1}$; $^1$H NMR (CDCl$_3$/TMS): δ 1.00 (d, J=6.9 Hz, 6 H, CH(CH$_3$)$_2$), 1.21 (t, J=7.1 Hz, 3 H, OCH$_2$CH$_3$), 2.33 (s, 3 H, CH$_3$), 3.35 (septet, J=6.9 Hz, 1 H, CH(CH$_3$)$_2$), 3.68 (q, J=7.1 Hz, 2 H, OCH$_2$CH$_3$), 6.27 (br s, 2 H, NCH$_2$O), 7.08–7.28 (m, 4 H, Ar H), 9.46 (br s, 1 H, NH)

Example 22

Preparation of 6-[(3,5-dimethylphenyl)selenenyl]-1-(ethoxymethyl)-5-isopropyl-2-thiouracil (Compound No. 24)

The titled compound was prepared in the same manner as described in Example 13 by using 1-(ethoxymethyl)-5-isopropyl-2-thiouracil and bis(3,5-dimethylphenyl) diselenide in place of 1-(ethoxymethyl)-5-ethyl-2-thiouracil and diphenyl diselenide, respectively.

Yield: 83%; IR (KBr): 1651 cm$^{-1}$; $^1$H NMR (CDCl$_3$/TMS): δ 1.01 (d, J=6.9 Hz, 6 H, CH(CH$_3$)$_2$), 1.21 (t, J=7.1 Hz, 3 H, OCH$_2$CH$_3$), 2.28 (s, 6 H, 2 CH$_3$), 3.35 (septet, J=6.9 Hz, 1 H, CH(CH$_3$)$_2$), 3.69 (q, J=7.1 Hz, 2 H, OCH$_2$CH$_3$), 6.27 (br s, 2 H, NCH$_2$O), 6.92 (s, 1 H, Ar H), 7.01 (s, 2 H, Ar H), 9.44 (br s, 1 H, NH)

Example 23

Preparation of 6-[(3,5-difluorophenyl)selenenyl]-1-(ethoxymethyl)-5-isopropyl-2-thiouracil (Compound No. 25)

The titled compound was prepared in the same manner as described in Example 13 by using 1-(ethoxymethyl)-5-isopropyl-2-thiouracil and bis(3,5-difluorophenyl) diselenide in place of 1-(ethoxymethyl)-5-ethyl-2-thiouracil and diphenyl diselenide, respectively.

Yield: 34%; IR (KBr): 1653 cm$^{-1}$; $^1$H NMR (CDCl$_3$/TMS): δ 1.09 (d, J=6.9 Hz, 6 H, CH(CH$_3$)$_2$), 1.18 (t, J=7.1 Hz, 3 H, OCH$_2$CH$_3$), 3.27 (septet, J=6.9 Hz, 1 H, CH(CH$_3$)$_2$), 3.68 (q, J=7.1 Hz, 2 H, OCH$_2$CH$_3$), 6.22 (br s, 2 H, NCH$_2$O), 6.76 (m, 1 H, Ar H), 6.95 (m, 2 H, Ar H), 9.52 (br s, 1 H, NH)

Example 24

Preparation of 1-[(benzyloxy)methyl]-5-isopropyl-6-(phenylselenenyl)-2-thiouracil (Compound No. 26)

The titled compound was prepared in the same manner as described in Example 13 by using 1-[(benzyloxy)methyl]-5-isopropyl-2-thiouracil in place of 1-(ethoxymethyl)-5-ethyl-2-thiouracil.

Yield: 39%; IR (KBr): 1700 cm$^{-1}$; $^1$H NMR (CDCl$_3$/TMS): δ 0.96 (d, J=6.9 Hz, 6 H, CH(CH$_3$)$_2$), 3.31 (septet, J=6.9 Hz, 1 H, CH(CH$_3$)$_2$), 4.73 (s, 2 H, CH$_2$Ph), 6.37 (br s, 2 H, NCH$_2$O), 7.28–7.40 (m, 10 H, Ar H), 9.35 (br s, 1 H, NH)

Example 25

Preparation of 1-[(benzyloxy)methyl]-5-isopropyl-6-[(3-methylphenyl) selenenyl]-2-thiouracil (Compound No. 27)

The titled compound was prepared in the same manner as described in Example 13 by using 1-[(benzyloxy)methyl]-5-isopropyl-2-thiouracil and bis(3-methylphenyl) diselenide in place of 1-(ethoxymethyl)-5-ethyl-2-thiouracil and diphenyl diselenide, respectively.

Yield: 51%; IR (KBr): 1698 cm$^{-1}$; $^1$H NMR (CDCl$_3$/TMS): δ 0.98 (d, J=6.9 Hz, 6 H, CH(CH$_3$)$_2$), 2.30 (s, 3 H, CH$_3$), 3.32 (septet, J=6.9 Hz, 1 H, CH(CH$_3$)$_2$), 4.73 (s, 2 H, CH$_2$Ph), 6.37 (br s, 2 H, NCH$_2$O), 7.08–7.40 (m, 9 H, Ar H), 9.37 (br s, 1 H, NH)

Example 26

Preparation of 1-[(benzyloxy)methyl]-6-[(3,5-dimethylphenyl)selenenyl]-5-isopropyl-2-thiouracil (Compound No. 28)

The titled compound was prepared in the same manner as described in Example 13 by using 1-[(benzyloxy)methyl]-5-isopropyl-2-thiouracil and bis(3,5-dimethylphenyl) diselenide in place of 1-(ethoxymethyl)-5-ethyl-2-thiouracil and diphenyl diselenide, respectively.

Yield: 20%; IR (KBr): 1645 cm$^{-1}$; $^1$H NMR (CDCl$_3$/TMS): δ 0.99 (d, J=6.9 Hz, 6 H, CH(CH$_3$)$_2$), 2.25 (s, 6 H, 2 CH$_3$), 3.33 (septet, J=6.9 Hz, 1 H, CH(CH$_3$)$_2$), 4.73 (s, 2 H, CH$_2$Ph), 6.37 (br s, 2 H, NCH$_2$O), 6.90 (s, 1 H, Ar H), 6.97 (s, 2 H, Ar H), 7.25–7.38 (m, 5 H, Ar H), 9.35 (br s, 1 H, NH)

Example 27

Preparation of 1-(ethoxymethyl)-5-ethyl-6-[(3-methylphenyl)selenenyl]uracil (Compound No. 29)

The titled compound was prepared in the same manner as described in Example 13 by using 1-(ethoxymethyl)-5-ethyluracil and bis(3-methylphenyl) diselenide in place of 1-(ethoxymethyl)-5-ethyl-2-thiouracil and diphenyl diselenide, respectively.

Yield: 56%; IR (KBr): 1706, 1670 cm$^{-1}$; $^1$H NMR (CDCl$_3$/TMS): δ 0.93 (t, J=7.4 Hz, 3 H, CH$_2$CH$_3$), 1.14 (t, J=7.1 Hz, 3 H, OCH$_2$CH$_3$), 2.32 (s, 3 H, CH$_3$), 2.67 (q, J=7.4 Hz, 2 H, CH$_2$CH$_3$), 3.57 (q, J=7.1 Hz, 2 H, OCH$_2$CH$_3$), 5.56 (s, 2 H, NCH$_2$O), 7.05–7.22 (m, 4 H, Ar H), 8.60 (br s, 1 H, NH)

Example 28

Preparation of 6-[(3,5-dimethylphenyl)selenenyl]-1-(ethoxymethyl)-5-etlyluracil (Compound No. 30)

The titled compound was prepared in the same manner as described in Example 13 by using 1-(ethoxymethyl)-5-ethyluracil and bis(3,5-dimethylphenyl) diselenide in place of 1-(ethoxymethyl)-5-ethyl-2-thiouracil and diphenyl diselenide, respectively.

Yield: 67%; IR (KBr): 1709, 1646 cm$^{-1}$; $^1$H NMR (CDCl$_3$/TMS): δ 0.94 (t, J=7.4 Hz, 3 H, CH$_2$CH$_3$), 1.16 (t, J=7.1 Hz, 3 H, OCH$_2$CH$_3$), 2.28 (s, 6 H, 2 CH$_3$), 2.68 (q, J=7.4 Hz, 2 H, CH$_2$CH$_3$), 3.58 (q, J=7.1 Hz, 2 H, OCH$_2$CH$_3$), 5.56 (s, 2 H, NCH$_2$O), 6.90 (s, 1 H, Ar H), 6.96 (s, 2 H, Ar H), 8.59 (br s, 1 H, NH)

Example 29

Preparation of 6-[(3,5-difluorophenyl)selenenyl]-1-(ethoxymethyl)-5-ethyluracil (Compound No. 32)

The titled compound was prepared in the same manner as described in Example 13 by using 1-(ethoxymethyl)-5-ethyluracil and bis(3,5-difluorophenyl) diselenide in place of 1-(ethoxymethyl)-5-ethyl-2-thiouracil and diphenyl diselenide, respectively.

Yield: 20%; IR (KBr): 1714, 1652 cm$^{-1}$; $^1$H NMR (CDCl$_3$/TMS): δ 0.99 (t, J=7.4 Hz, 3 H, CH$_2$CH$_3$), 1.11 (t, J=6.9 Hz, 3 H, OCH$_2$CH$_3$), 2.66 (q, J=7.4 Hz, 2 H, CH$_2$CH$_3$), 3.57 (q, J=6.9 Hz, 2 H, OCH$_2$CH$_3$), 5.55 (s, 2 H, NCH$_2$O), 6.73 (m, 1 H, Ar H), 6.88 (m, 2 H, Ar H), 9.41 (br s, 1 H, NH)

Example 30

Preparation of 1-[(benzyloxy)methyl]-5-ethyl-6-[(3-methylphenyl)selenenyl]uracil (Compound No. 37)

The titled compound was prepared in the same manner as described in Example 13 by using 1-[(benzyloxy)methyl]-5-ethyluracil and bis(3-methylphenyl) diselenide in place of 1-(ethoxymethyl)-5-ethyl-2-thiouracil and diphenyl diselenide, respectively.

Yield: 33%; IR (KBr): 1704, 1671 cm$^{-1}$; $^1$H NMR (CDCl$_3$/TMS): δ 0.92 (t, J=7.4 Hz, 3 H, CH$_2$CH$_3$), 2.28 (s, 3 H, CH$_3$) 2.64 (q, J=7.4 Hz, 2 H, CH$_2$CH$_3$), 4.63 (s, 2 H, CH$_2$Ph), 5.64 (s, 2 H, NCH$_2$O), 7.04–7.36 (m, 9 H, Ar H), 8.46 (br s, 1 H, NH)

Example 31

Preparation of 1-[(benzyloxy)methyl]-6-[(3,5-dimethylphenyl)selenenyl]-5-ethyluracil (Compound No. 38)

The titled compound was prepared in the same manner as described in Example 13 by using 1-[(benzyloxy)methyl]-5-ethyluracil and bis(3,5-dimethylphenyl) diselenide in place of 1-(ethoxymethyl)-5-ethyl-2-thiouracil and diphenyl diselenide, respectively.

Yield: 20%; IR (KBr): 1708, 1667 cm$^{-1}$; $^1$H NMR (CDCl$_3$/TMS): δ 0.92 (t, J=7.4 Hz, 3 H, CH$_2$CH$_3$), 2.24 (s, 6 H, 2 CH$_3$), 2.64 (q, J=7.4 Hz, 2 H, CH$_2$CH$_3$), 4.64 (s, 2 H, CH$_2$Ph), 5.64 (s, 2 H, NCH$_2$O), 6.88 (s, 1 H, Ar H), 6.91 (s, 2 H, Ar H), 7.24–7.35 (m, 5 H, Ar H), 8.30 (br s, 1 H, NH)

Example 32

Preparation of 1-(ethoxymethyl)-5-isopropyl-6-(phenylselenenyl)uracil (Compound No. 48)

To a stirred suspension of 1-(ethoxymethyl)-5-isopropyl-6-(phenylselenenyl)-2-thiouracil (0.26 g, 0.68 mmol) in aquous 1N NaOH (6 mL) was added 35% H$_2$O$_2$ (0.40 mL, 4.08 mmol). After the mixture was stirred at room temperature for 1 h, the reaction mixture was neutralized with concentrated HCl. The resulting precipitate was filtered and washed well with saturated NaHCO$_3$ solution (3×5 mL) and H$_2$O (3×5 mL). The precipitate was thoroughly dried in vacua over P$_2$O$_5$ and crystallized from EtOAc-hexane to give 0.22 g (88%) of the target compound IR (KBr): 1712, 1644 cm$^{-1}$; $^1$H NMR (CDCl$_3$/TMS): δ 1.07 (d, J=6.9 Hz, 6 H, CH(CH$_3$)$_2$), 1.16 (t, J=7.1 Hz, 3 H, OCH$_2$CH$_3$), 3.42 (septet, J=6.9 Hz, 1 H, CH(CH$_3$)$_2$), 3.59 (q, J=7.1 Hz, 2 H, OCH$_2$CH$_3$), 5.64 (s, 2 H, NCH$_2$O), 7.26–7.43 (m, 5 H, Ar H), 8.54 (br s, 1 H, NH)

Example 33

Preparation of 1-(ethoxymethyl)-5-isopropyl-6-[(3-methylphenyl)selenenyl]uracil (Compound No. 49)

The titled compound was prepared in the same manner as described in Example 32 by using 1-(ethoxymethyl)-5-isopropyl-6-[(3-methylphenyl)selenenyl]-2-thiouracil in place of 1-(ethoxymethyl)-5-isopropyl-6-(phenylselenenyl)-2-thiouracil.

Yield: 75%; IR (KBr): 1711, 1645 cm$^{-1}$; $^1$H NMR (CDCl$_3$/TMS): δ 1.08 (d, J=6.9 Hz, 6 H, CH(CH$_3$)$_2$), 1.17 (t, J=7.1 Hz, 3 H, OCH$_2$CH$_3$), 2.32 (s, 3 H, CH$_3$), 3.42 (septet, J=6.9 Hz, 1 H, CH(CE$_3$)$_2$), 3.59 (q, J=7.1 Hz, 2 H, OCH$_2$CH$_3$), 5.64 (s, 2 H, NCH$_2$O), 7.05–7.23 (m, 4 H, Ar H), 8.63 (br s, 1 H, NH)

Example 34-A

Preparation of 6-[(3,5-dimethylphenyl)selenenyl]-1-(ethoxymethyl)-5-isopropyluracil (Compound No. 50)

The titled compound was prepared in the same manner as described in Example 32 by using 6-[(3,5-dimethylphenyl)selenenyl]-1-(ethoxymethyl)-5-isopropyl-2-thiouracil in place of 1-(ethoxymethyl)-5-isopropyl-6-(phenylselenenyl)-2-thiouracil.

Yield: 88%; IR (KBr): 1711, 1645 cm$^{-1}$; $^1$H NMR (CDCl$_3$/TMS): δ 1.09 (d, J=6.9 Hz, 6 H, CH(CH$_3$)$_2$), 1.18 (t, J=7.1 Hz, 3 H, OCH$_2$CH$_3$), 2.28 (s, 6 H, 2 CH$_3$), 3.43 (septet, J=6.9 Hz, 1 H, CH(CH$_3$)$_2$), 3.59 (q, J=7.1 Hz, 2 H, OCH$_2$CH$_3$), 5.64 (s, 2 H, NCH$_2$O), 6.90 (s, 1 H, Ar H), 6.99 (s, 2 H, Ar H), 8.43 (br s, 1 H, NH)

Example 34-B

Preparation of 6-[(3,5-dimethylphenyl)selenenyl]-1-(ethoxymethyl)-5-isopropyluracil (Compound No. 50)

To a solution of 6-chloro-1-(ethoxymethyl)-5-isopropyluracil (1.00 g, 4.06 mmol) in absolute EtOH (15 mL) at room temperature under a nitrogen atmosphere was added 1N ethanolic NaOH solution (4.26 mmol, 4.3 mL) followed by dropwise addition of 3,5-dimethylphenyl selenol (789 mg, 4.26 mmol, 0.61 mL) via a syringe and the resulting slurry was stirred at room temperature for 2 h. The reaction mixture was cooled to 0° C., a white precipitate was collected and was washed with cold EtOH. The resulting white solid was dissolved in CH$_2$Cl$_2$ and insoluble NaCl was removed by passing through a Celite pad. Evaporation to dryness gave a white crystalline product (1.31 g, 82%). The ethanolic portion was acidified with concentrated HCl to pH=5–6 and was evaporated to dryness to afford a yellow residue. Brine (30 mL) was added to the residue, extracted with CH$_2$Cl$_2$ (2×20 mL), dried over anhydrous MgSO$_4$, and was evaporated to dryness to obtain a yellow oil. The crude oil was purified by flash column chromatography on silica gel with EtOAc-hexane (1:2) as eluent to give an additional white solid (285 mg, 18%). Crystallization from EtOAc-hexane gave an analytically pure product.

Example 35

Preparation of 6-[(3,5-difluorophenyl)selenenyl]-1-(ethoxymethyl)-5-isopropyluracil (Compound No. 51)

The titled compound was prepared in the same manner as described in Example 32 by using 6-[(3,5-difluorophenyl)selenenyl]-1-(ethoxymethyl)-5-isopropyl-2-thiouracil in place of 1-(ethoxymethyl)-5-isopropyl-6-(phenylselenenyl)-2-thiouracil.

Yield: 82%; IR (KBr): 1703, 1673 cm$^{-1}$; $^1$H NMR (CDCl$_3$/TMS): δ 1.14 (t, J=7.1 Hz, 3 H, OCH$_2$CH$_3$), 1.15 (d, J=6.9Hz, 6 H, CH(CH$_3$)$_2$), 3.35 (septet, J=6.9 Hz, 1 H, CH(CH$_3$)$_2$), 3.58 (q, J=7.1 Hz, 2 H, OCH$_2$CH$_3$), 5.59 (s, 2 H, NCH$_2$O), 6.74 (m, 1 H, Ar H), 6.93 (m, 2 H, Ar H), 8.48 (br s, 1 H, NH)

Example 36-A

Preparation of 1-[(benzyloxy)methyl]-5-isopropyl-6-(phenylselenenyl)uracil (Compound No. 52)

The titled compound was prepared in the same manner as described in Example 32 by using 1-[(benzyloxy)methyl]-5-isopropyl-6-(phenylselenenyl)-2-thiouracil in place of 1-(ethoxymethyl)-5-isopropyl-6-(phenylselenenyl)-2-thiouracil.

Yield: 36%; IR (KBr): 1709, 1642 cm$^{-1}$; $^1$H NMR (CDCl$_3$/TMS): δ 1.05 (d, J=6.9 Hz, 6 H, CH(CH$_3$)$_2$), 3.39 (septet, J=6.9 Hz, 1 H, CH(CH$_3$)$_2$), 4.64 (s, 2 H, CH$_2$Ph), 5.73 (s, 2 H, NCH$_2$O), 7.25–7.40 (m, 10 H, Ar H), 8.09 (br s, 1 H, NH)

Example 36-B

Preparation of 1-[(benzyloxy)methyl]-5-isopropyl-6-(phenylselenenyl)uracil (Compound No. 52)

The titled compound was prepared in the same manner as described in Example 34 B by using 1-[(benzyloxy)methyl]-6-chloro-5-isopropyluracil and benzeneselenol in place of 6-chloro-1-(ethoxymethyl)-5-isopropyluracil and 3,5-dimethylphenyl selenol.

Yield: 92%;

Example 37

Preparation of 1-[(benzyloxy)methyl]-5-isopropyl-6-[(3-methylphenyl)selenenyl]uracil (Compound No. 53)

The titled compound was prepared in the same manner as described in Example 32 by using 1-[(benzyloxy)methyl]-5-isopropyl-6-[(3-methylphenyl)selenenyl]-2-thiouracil in place of 1-(ethoxymethyl)-5-isopropyl-6-(phenylselenenyl)-2-thiouracil.

Yield: 30%; IR (KBr): 1684 cm$^{-1}$; $^1$H NMR (CDCl$_3$/TMS): δ 1.07 (d, J=6.9 Hz, 6 H, CH(CH$_3$)$_2$), 2.28 (s, 3 H, CH$_3$), 3.40 (septet, J=6.9 Hz, 1 H, CH(CH$_3$)$_2$), 4.64 (s, 2 H, CH$_2$Ph), 5.74 (s, 2 H, NCH$_2$O), 7.03–7.37 (m, 9 H, Ar H), 8.80 (br s, 1 H, NH)

Example 38-A

Preparation of 1-[(benzyloxy)methyl]-6-[(3,5-dimethylphenyl)selenenyl]-5-isopropyluracil (Compound No. 54)

The titled compound was prepared in the same manner as described in Example 32 by using 1-[(benzyloxy)methyl]-6-[(3,5-dimethylphenyl)selenenyl]-5-isopropyl-2-thiouracil in place of 1-(ethoxymethyl)-5-isopropyl-6-(phenylselenenyl)-2-thiouracil.

Yield: 15%; IR (KBr): 1708, 1645 cm$^{-1}$; $^1$H NMR (CDCl$_3$/TMS): δ 1.08 (d, J=6.9 Hz, 6 H, CH(CH$_3$)$_2$), 2.24 (s, 6 H, 2 CH$_3$), 3.41 (septet, J=6.9 Hz, 1 H, CH(CH$_3$)$_2$), 4.64 (s, 2 H, CH$_2$Ph), 5.73 (s, 2 H, NCH$_2$O), 6.88 (s, 1 H, Ar H), 6.96 (s, 2 H, Ar H), 7.26–7.37 (m, 5 H, Ar H), 8.81 (br s, 1 H, NH)

Example 38-B

Preparation of 1-[(benzyloxy)methyl]-6-[(3,5-dimethylphenyl)selenenyl]-5-isopropyluracil (Compound No. 54)

The titled compound was prepared in the same manner as described in Example 34 B by using 1-[(benzyloxy)methyl]-6-chloro-5-isopropyluracil in place of 6-chloro-1-(ethoxymethyl)-5-isopropyluracil.

Yield: 100%;

Example 39

Preparation of 5-ethyl-1-(4-hydroxybutyl)-6-(phenylselenenyl)-2-thiouracil (Compound No. 55)

To a stirred suspension of 1-(4-acetoxybutyl)-5-ethyl-6-(methylsulfinyl)-2-thiouracil (0.33 g, 1.00 mmol) and benzeneselenol (0.11 mL, 1.04 mmol) in EtOH (5 mL) was added 1N methanolic NaOH solution (3.00 mL) at room temperature under a nitrogen atmosphere. After the mixture was stirred for 2 h, 3N HCl in EtOH (1.00 mL) was added and the reaction mixture was evaporated to dryness. The residue was purified by flash column chromatography on silica gel with MeOH-CHCl$_3$ (5:95) as eluent to give 0.23 g of the titled compound.

Yield: 60%; IR (KBr): 1586 (CO), 3447 (OH) cm$^{-1}$; $^1$H NMR (CDCl$_3$/TMS): δ 1.12 (t, J=7.4 Hz, 3 H, CH$_2$CH$_3$), 1.57 (m, 2 H, NCH$_2$CH$_2$), 1.67 (m, 2 H, NCH$_2$CH$_2$CH$_2$), 2.84 (q, J=7.4 Hz, 2 H, CH$_2$CH$_3$), 3.34 (br s, 2 H, NCH$_2$), 3.63 (t, J=5.9 Hz, 2 H, CH$_2$OH), 7.32–7.47 (m, 3 H, Ar H), 7.57–7.66 (m, 2 H, Ar H)

Example 40

Preparation of 6-[(3,5-dimethylphenyl)selenenyl]-5-ethyl-1-(4-hydroxybutyl)-2-thiouracil (Compound No. 57)

The titled compound was prepared in the same manner as described in Example 39 by using 3,5-dimethylphenyl selenol in place of benzeneselenol.

Yield: 64%; IR (KBr): 1596 (CO), 3450 (OH) cm$^{-1}$; $^1$H NMR (CDCl$_3$/TMS): δ 1.12 (t, J=7.4 Hz, 3 H, CH$_2$CH$_3$), 1.58 (m, 2 H, NCH$_2$CH$_2$), 1.68 (m, 2 H, NCH$_2$CH$_2$CH$_2$), 2.33 (s, 6 H, 2 CH$_3$), 2.83 (q, J=7.4 Hz, 2 H, CH$_2$CH$_3$), 3.37 (br s, 2 H, NCH$_2$), 3.64 (t, J=5.9 Hz, 2 H, CH$_2$OH), 7.04 (s, 1 H, Ar H), 7.22 (s, 2 H, Ar H)

Example 41

Preparation of 1-(4-hydroxybutyl)-5-isopropyl-6-(phenylselenenyl)-2-thiouracil (Compound No. 58)

The titled compound was prepared in the same manner as described in Example 39 by using 1-(4-acetoxybutyl)-5-isopropyl-6-(methylsulfinyl)-2-thiouracil in place of 1-(4-acetoxybutyl)-5-ethyl-6-(methylsulfinyl)-2-thiouracil.

Yield: 69%; IR (KBr): 1558, 1611 (CO), 3209 (OH) cm$^{-1}$; $^1$H NMR (CDCl$_3$/TMS): δ 1.31 (d, J=6.8 Hz, 6 H, CH(CH$_3$)$_2$), 1.55 (m, 2 H, NCH$_2$CH$_2$), 1.66 (m, 2 H, NCH$_2$CH$_2$CH$_2$), 3.34 (br s, 2 H, NCH$_2$), 3.49 (septet, J=6.8 Hz, 1 H, CH(CH$_3$)$_2$), 3.64 (t, J=5.9 Hz, 2 H, CH$_2$OH), 7.28–7.45 (m, 3 H, Ar H), 7.57–7.63 (m, 2 H, Ar H)

Example 42

Preparation of 6-[(3,5-dimethylphenyl)selenenyl]-1-(4-hydroxybutyl)-5-isopropyl-2-thiouracil (Compound No. 60)

The titled compound was prepared in the same manner as described in Example 39 by using 1-(4-acetoxybutyl)-5-isopropyl-6-(methylsulfinyl)-2-thiouracil and (3,5-dimethylphenyl)selenol in place of 1-(4-acetoxybutyl)-5-ethyl-6-(methylsulfinyl)-2-thiouracil and benzeneselenol, respectively.

Yield: 62%; IR (KBr): 1558, 1615 (CO), 3208 (OH) cm$^{-1}$; $^1$H NMR (CDCl$_3$/TMS): δ 1.32 (d, J=6.9 Hz, 6 H, CH(CH$_3$)$_2$), 1.57 (m, 2 H, NCH$_2$CH$_2$), 1.68 (m, 2 H, NCH$_2$CH$_2$CH$_2$), 2.32 (s, 6 H, 2 CH$_3$), 3.36 (br s, 2 H, NCH$_2$), 3.48 (septet, J=6.9 Hz, 1 H, CH(CH$_3$)$_2$), 3.65 (t, J=5.9 Hz, 2 H, CH$_2$OH), 7.03 (s, 1 H, Ar H), 7.21 (s, 2 H, Ar H)

Example 43

Preparation of 1-butyl-5-isopropyl-6-(phenylselenenyl)-2-thiouracil (Compound No. 61)

The titled compound was prepared in the same manner as described in Example 39 by using 1-butyl-5-isopropyl-6-(methylsulfinyl)-2-thiouracil in place of 1-(4-acetoxybutyl)-5-ethyl-6-(methylsulfinyl)-2-thiouracil.

Yield: 83%; IR (KBr): 1601, 1622 (CO) cm$^{-1}$; $^1$H NMR (CDCl$_3$/TMS): δ 0.87 (t, J=7.4 Hz, 3 H, NCH$_2$CH$_2$CH$_2$CH$_3$), 1.30 (m, 2 H, NCH$_2$CH$_2$CH$_2$), 1.33 (d, J=6.9 Hz, 6 H, CH(CH$_3$)$_2$), 1.51 (m, 2 H, NCH$_2$CH$_2$), 3.29 (br s, 2 H, NCH$_2$), 3.49 (septet, J=6.9 Hz, 1 H, CH(CH$_3$)$_2$), 7.30–7.46 (m, 3 H, Ar H), 7.54–7.66 (m, 2 H, Ar H)

Example 44

Preparation of 1-butyl-6-[(3,5-dimethylphenyl)selenenyl]-5-isopropyl-2-thiouracil (Compound No. 63)

The titled compound was prepared in the same manner as described in Example 39 by using 1-butyl-5-isopropyl-6-(methylsulfinyl)-2-thiouracil and (3,5-dimethylphenyl) selenol in place of 1-(4-acetoxybutyl)-5-ethyl-6-(methylsulfinyl)-2-thiouracil and benzeneselenol, respectively.

Yield: 88%; IR (KBr): 1592, 1616 (CO) cm$^{-1}$; $^1$H NMR (CDCl$_3$/TMS): δ 0.88 (t, J=7.4 Hz, 3 H, NCH$_2$CH$_2$CH$_2$CH$_3$), 1.30 (m, 2 H, NCH$_2$CH$_2$CH$_2$), 1.34 (d, J=6.8 Hz, 6 H, CH(CH$_3$)$_2$), 1.52 (m, 2 H, NCH$_2$CH$_2$), 2.32 (s, 6 H, 2 CH$_3$), 3.32 (br s, 2 H, NCH$_2$), 3.46 (septet, J=6.8 Hz, 1 H, CH(CH$_3$)$_2$), 7.04 (s, 1 H, Ar H), 7.22 (s, 2 H, Ar H)

Example 45

Preparation of 1-butyl-5-ethyl-6-(phenylselenenyl)uracil (Compound No. 64)

The titled compound was prepared in the same manner as described in Example 39 by using 1-butyl-5-ethyl-6-(methylsulfonyl)uracil in place of 1-(4-acetoxybutyl)-5-ethyl-6-(methylsulfinyl)-2-thiouracil.

Yield: 95%; IR (KBr): 1654, 1706 (CO) cm$^{-1}$; $^1$H NMR (CDCl$_3$/TMS): δ 0.87 (t, J=7.2 Hz, 3 H, NCH$_2$CH$_2$CH$_2$CH$_3$), 1.03 (t, J=7.4 Hz, 3 H, CH$_2$CH$_3$), 1.26 (m, 2 H, NCH$_2$CH$_2$CH$_2$), 1.51 (m, 2 H, NCH$_2$CH$_2$), 2.75 (q, J=7.4 Hz, 2 H, CH$_2$CH$_3$), 4.03 (t, J=8.0 Hz, 2 H, NCH$_2$), 7.31 (m, 5 H, Ar H), 8.74 (br s, 1 H, NH)

Example 46

Preparation of 1-butyl-6-[(3,5-dimethylphenyl)selenenyl]-5-ethyluracil (Compound No. 65)

The titled compound was prepared in the same manner as described in Example 39 by using 1-butyl-5-ethyl-6-(methylsulfonyl)uracil and (3,5-dimethylphenyl)selenol in place of 1-(4-acetoxybutyl)-5-ethyl-6-(methylsulfinyl)-2-thiouracil and benzeneselenol, respectively.

Yield: 94%; IR (KBr): 1662, 1701 (CO) cm$^{-1}$; $^1$H NMR (CDCl$_3$/TMS): δ 0.87 (t, J=7.2 Hz, 3 H, NCH$_2$CH$_2$CH$_2$CH$_3$), 1.04 (t, J=7.4 Hz, 3 H, CH$_2$CH$_3$), 1.26 (m, 2 H, NCH$_2$CH$_2$CH$_2$), 1.49 (m, 2 H, NCH$_2$CH$_2$), 2.28 (s, 6 H, 2 CH$_3$), 2.76 (q, J=7.4 Hz, 2 H, CH$_2$CH$_3$), 4.04 (t, J=8.0 Hz, 2 H, NCH$_2$), 6.92 (s, 3 H, Ar H), 8.68 (br s, 1 H, NH)

Example 47

Preparation of 1-butyl-5-ethyl-6-(phenylselenenyl)-2-thiouracil (Compound No. 66)

The titled compound was prepared in the same manner as described in Example 39 by using 1-butyl-5-ethyl-6-(methylsulfinyl)-2-thiouracil in place of 1-(4-acetoxybutyl)-5-ethyl-6-(methylsulfinyl)-2-thiouracil.

Yield: 76%; IR (KBr); 1604 (CO) cm$^{-1}$; $^1$H NMR (CDCl$_3$/TMS): δ 0.88 (t, J=7.4 Hz, 3 H, NCH$_2$CH$_2$CH$_2$CH$_3$), 1.14 (t, J=7.4 Hz, 3 H, CH$_2$CH$_3$), 1.30 (m, 2 H, NCH$_2$CH$_2$CH$_2$), 1.51 (m, 2 H, NCH$_2$CH$_2$), 2.86 (q, J=7.4 Hz, 2 H, CH$_2$CH$_3$), 3.32 (br s, 2 H, NCH$_2$), 7.31–7.48 (m, 3 H, Ar H), 7.58–7.66 (m, 2 H, Ar H)

Example 48

Preparation of 1-butyl-6-[(3,5-dimethylphenyl)selenenyl]-5-ethyl-2-thiouracil (Compound No. 68)

The titled compound was prepared in the same manner as described in Example 39 by using 1-butyl-5-ethyl-6-(methylsulfinyl)-2-thiouracil and (3,5-dimethylphenyl)selenol in place of 1-(4-acetoxybutyl)-5-ethyl-6-(methylsulfinyl)-2-thiouracil and benzeneselenol, respectively.

Yield: 74%; IR (KBr): 1609 (CO) cm$^{-1}$; $^1$H NMR (CDCl$_3$/TMS): δ 0.88 (t, J=7.4 Hz, 3 H, NCH$_2$CH$_2$CH$_2$CH$_3$), 1.14 (t, J=7.4 Hz, 3 H, CH$_2$CH$_3$), 1.32 (m, 2 H, NCH$_2$CH$_2$CH$_2$), 1.52 (m, 2 H, NCH$_2$CH$_2$), 2.33 (s, 6 H, 2 CH$_3$), 2.85 (q, J=7.4 Hz, 2 H, CH$_2$CH$_3$), 3.33 (br s, 2 H, NCH$_2$), 7.05 (s, 1 H, Ar H), 7.23 (s, 2 H, Ar H)

Example 49

Preparation of 5-ethyl-1-(3-phenylpropyl)-6-(phenylselenenyl)uracil (Compound No. 73)

The titled compound was prepared in the same manner as described in Example 39 by using 5-ethyl-6-(methylsulfonyl)-1-(3-phenylpropyl)uracil in place of 1-(4-acetoxybutyl)-5-ethyl-6-(methylsulfinyl)-2-thiouricil.

Yield: 96%; IR (KBr): 1675, 1684 (CO) cm$^{-1}$; $^1$H NMR (CDCl$_3$/TMS): δ 1.04 (t, J=7.4 Hz, 3 H, CH$_2$CH$_3$), 1.91 (tt, J=7.8 Hz, J=7.5 Hz, 2 H, NCH$_2$CH$_2$), 2.60 (t, J=7.5 Hz, 2 H, CH$_2$Ph), 2.74 (q, J=7.4 Hz. 2 H, CH$_2$CH$_3$), 4.03 (t, J=7.8 Hz, 2 H, NCH$_2$), 7.07–7.32 (m, 10 H, Ar H), 8.56 (br s, 1 H, NH)

Example 50

Preparation of 6-[(3,5-dimethylphenyl)selenenyl]-5-ethyl-1-(3-phenylpropyl)-uracil (Compound No. 74)

The titled compound was prepared in the same manner as described in Example 39 by using 5-ethyl-6-(methylsulfonyl)-1-(3-phenylpropyl)uracil and (3,5-dimethylphenyl)selenol in place of 1-(4-acetoxybutyl)-5-ethyl-6-(methylsulfinyl)-2-thiouracil and benzeneselenol, respectively.

Yield: 98%; IR (KBr): 1664, 1716 (CO) cm$^{-1}$; $^1$H NMR (CDCl$_3$/TMS): δ 1.04 (t, J=7.4 Hz, 3 H, CH$_2$CH$_3$), 1.92 (tt, J=8.0 Hz, J =7.7 Hz, 2 H, NCH$_2$CH$_2$), 2.26 (s, 6 H, 2 CH$_3$), 2.60 (t, J=7.7 Hz, 2 H, CH$_2$Ph), 2.75 (q, J=7.4 Hz, 2 H, CH$_2$CH$_3$), 4.04 (t, J=8.0 Hz, 2 H, NCH$_2$), 6.78 (s, 2 H, Ar H), 6.89 (s, 1 H, Ar H), 7.08–7.30 (m, 5 H, Ar H), 8.49 (br s, 1 H, NH)

Example 51

Preparation of 1-butyl-5-isopropyl-6-(phenylselenenyl)uracil (Compound No. 81)

The titled compound was prepared in the same manner as described in Example 39 by using 1-butyl-5-isopropyl-6-(methylsulfonyl)uracil in place of 1-(4-acetoxybutyl)-5-ethyl-6-(methylsulfinyl)-2-thiouracil.

Yield: 98%; IR (KBr): 1652, 1701 (CO) cm$^{-1}$; $^1$H NMR (CDCl$_3$/TMS): δ 0.89 (t, J=7.4 Hz, 3 H, NCH$_2$CH$_2$CH$_2$CH$_3$), 1.19 (d, J=6.9 Hz, 6 H, CH(CH$_3$)$_2$), 1.30 (m, 2 H, NCH$_2$CH$_2$CH$_2$), 1.56 (m, 2 H, NCH$_2$CH$_2$), 3.51 (septet, J=6.9 Hz, 1 H, CH(CH$_3$)$_2$), 4.11 (t, J=8.0 Hz, 2 H, NCH$_2$), 7.25–7.40 (m, 5 H, Ar H), 8.49 (br s, 1 H, NH)

Example 52

Preparation of 1-butyl-6-[(3,5-dimethylphenyl)selenenyl]-5-isopropyluracil (Compound No. 83)

The titled compound was prepared in the same manner as described in Example 39 by using 1-butyl-5-isopropyl-6-(methylsulfonyl)uracil and (3,5-dimethylphenyl)selenol in place of 1-(4-acetoxybutyl)-5-ethyl-6-(methylsulfinyl)-2-thiouracil and benzeneselenol, respectively.

Yield: 99%; IR (KBr): 1682, 1694 (CO) cm$^{-1}$; $^1$H NMR (CDCl$_3$/TMS): δ 0.89 (t, J=7.2 Hz, 3 H, NCH$_2$CH$_2$CH$_2$CH$_3$), 1.21 (d, J=6.9 Hz, 6 H, CH(CH$_3$)$_2$), 1.29 (m, 2 H, NCH$_2$CH$_2$CH$_2$), 1.54 (m, 2 H, NCH$_2$CH$_2$), 2.28 (s, 6 H, 2 CH$_3$), 3.52 (septet, J=6.9 Hz, 1 H, CH(CH$_3$)$_2$), 4.11 (t, J=8.0 Hz, 2 H, NCH$_2$), 6.93 (m, 3 H, Ar H), 8.52 (br s, 1 H, NH)

Example 53

Preparation of 5-isopropyl-1-(3-phenylpropyl)-6-(phenylselenenyl)uracil (Compound No. 84)

The titled compound was prepared in the same manner as described in Example 39 by using 5-isopropyl-6-(methylsulfonyl)-1-(3-phenylpropyl)uracil in place of 1-(4-acetoxybutyl)-5-ethyl-6-(methylsulfinyl)-2-thiouracil.

Yield: 99%; IR (KBr): 1663, 1698 (CO) cm$^{-1}$; $^1$H NMR (CDCl$_3$/TMS): δ 1.21 (d, J=6.9 Hz, 6 H, CH(CH$_3$)$_2$), 1.94 (tt, J=8.0 Hz, J=7.5 Hz, 2 H, NCH$_2$CH$_2$), 2.62 (t, J=7.5 Hz, 2 H, CH$_2$Ph), 3.51 (septet, J=6.9 Hz, 1 H, CH(CH$_3$)$_2$), 4.11 (t, J=8.0 Hz, 2 H, NCH$_2$), 7.10–7.35 (m, 10 H, Ar H), 8.47 (br s, 1 H, NH)

Example 54

Preparation of 6-[(3,5-dimethylphenyl)selenenyl]-5-isopropyl-1-(3-phenylpropyl)-uracil (Compound No. 86)

The titled compound was prepared in the same manner as described in Example 39 by using 5-isopropyl-6-(methylsulfonyl)-1-(3-phenylpropyl)uracil and (3,5-dimethylphenyl)selenol in place of 1-(4-acetoxybutyl)-5-ethyl-6-(methylsulfinyl)-2-thiouracil and benzeneselenol, respectively.

Yield: 99%; IR (KBr): 1668, 1698 (CO) cm$^{-1}$; $^1$H NMR (CDCl$_3$/TMS): δ 1.22 (d, J=6.9 Hz, 6 H, CH(CH$_3$)$_2$), 1.94 (tt, J=8.0 Hz, J=7.7 Hz, 2 H, NCH$_2$CH$_2$), 2.26 (s, 6 H, 2 CH$_3$), 2.62 (t, J=7.7 Hz, 2 H, CH$_2$Ph), 3.51 (septet, J=6.9 Hz, 1 H, CH(CH$_3$)$_2$), 4.12 (t, J=8.0 Hz, 2 H, NCH$_2$), 6.81 (s, 2 H, Ar H), 6.89 (s, 1 H, Ar H), 7.10–7.32 (m, 5 H, Ar H), 8.40 (br s, 1 H, NH)

Example 55

| Production of tablet | |
|---|---|
| 6-[(3,5-Dimethylphenyl)selenenyl]-1-(ethoxymethyl)-5-isopropyluracil (Compound No. 50) | 10 g |
| Lactose | 70 g |
| Crystalline cellulose | 15 g |
| Magnesium stearate | 5 g |
| Total weight | 100 g |

The above-mentioned components were well mixed and tablets were produced by a direct tableting method. Each tablet had a weight of 100 mg and contained 10 mg of 6-[(3,5-dimethylphenyl)selenenyl]-1-(ethoxymethyl)-5-isopropyluracil.

Example 56

| Production of powder and encapsulated medicine | |
|---|---|
| 6-[(3,5-Dimethylphenyl)selenenyl]-1-(ethoxymethyl)-5-isopropyluracil (Compound No. 50) | 10 g |
| Corn starch | 50 g |
| Carboxycellulose | 40 g |
| Total weight | 100 g |

The above-mentioned components were well mixed to obtain a powder general formulation. Capsule was obtained by encapsulating 100 mg of the thus obtained powder into a hard capsule of No. 5.

Example 57

Inhibitory Activity for HIV-induced Cytopathogenicity

In RPMI 1640 culture medium supplemented with 10% heat-inactivated fetal bovine serum, 2 mM of L-glutamine, 100 U/mL of penicillin G and 100 μg/mL of streptomycin, MT-4 cells (HTLV-1 transformed T4-cell line) at a concentration of 1×10$^4$/well in a flat-bottom, microtiter plate were infected with 500 TCID$_{50}$ of HIV-1 (HTLV-III$_B$ strain). Immediately after virus infection, sample serially diluted with culture medium from stock solution prepared in dimethyl sulfoxide was added to each well in quadriplicate. After 6 days incubation at 37° C., the viability of mock and HIV-infected cells was determined by the 3-(4,5-dimethylthiazol-2-yl)-2,5-diphenyltetrazolium bromide (MTT) method. And also, the cytotoxicity of sample to MT-4 cells not infected with HIV was assessed in parallel with its antiviral activity under the same way as above. These results are presented in Table 2.

TABLE 2

| Compound No. | 50% inhibitory concentration of HIV infection (μM) | 50% cytotoxic concentration to MT-4 cells (μM) |
|---|---|---|
| 2 | 0.04 | 32.0 |
| 3 | 0.03 | 32.5 |
| 5 | 0.038 | 31.7 |
| 6 | 0.008 | 32.4 |
| 9 | 0.015 | 34.5 |
| 11 | 0.015 | 30.5 |
| 12 | 0.0019 | 29.1 |
| 15 | 0.024 | 26.1 |
| 16 | 0.008 | 24.8 |
| 17 | 0.008 | 28.8 |
| 18 | 0.014 | 7.8 |
| 19 | 0.004 | 25.1 |
| 20 | 0.0008 | 43.4 |
| 21 | 0.0017 | 24.1 |
| 22 | 0.0015 | 30.1 |
| 23 | 0.0036 | 30.6 |
| 24 | 0.0016 | 31.7 |
| 25 | 0.027 | 19.7 |
| 26 | 0.0007 | 30.2 |
| 27 | 0.0011 | 30.0 |
| 28 | 0.0054 | 30.9 |
| 29 | 0.004 | 32.1 |
| 30 | 0.0006 | 28.9 |
| 32 | 0.006 | 30.6 |
| 37 | 0.00021 | 28.8 |
| 38 | 0.00008 | 31.7 |
| 48 | 0.0042 | 32.5 |
| 49 | 0.0007 | 29.2 |
| 50 | 0.00007 | 29.2 |
| 51 | 0.0012 | 27.5 |
| 52 | 0.0001 | 29.4 |
| 53 | 0.00007 | 30.8 |
| 54 | 0.000021 | 30.2 |
| 64 | 0.04 | 27.3 |
| 65 | 0.003 | 27.9 |
| 73 | 0.003 | 26.1 |
| 74 | 0.008 | 27.7 |
| 81 | 0.002 | 27.1 |
| 83 | 0.002 | 28.2 |
| 84 | 0.008 | 28.0 |
| 86 | 0.0006 | 26.9 |
| AZT | 0.0046 | 22.7 |
| DDC | 0.60 | 17.6 |

We claim:

1. A compound represented by the following formula (I):

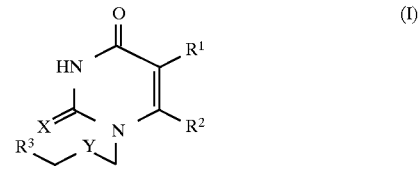

wherein R$^1$ is ethyl or isopropyl;
R$^2$ is (3,5 dimethylphenyl)selenenyl;
R$^3$ is phenyl or methyl;
X is oxygen;
Y is oxygen;
or a pharmaceutically acceptable salt thereof.

2. The compound according to claim 1 comprising 6-[3,5-dimethylphenyl)selenenyl]-1-(ethoxymethyl)-5-ethyluracil or a pharmaceutically acceptable salt thereof.

3. The compound according to claim 1 comprising 1-[(benzyloxy)methyl]-6-[(3,5-dimethylphenyl)selenenyl]-5-ethyluracil or a pharmaceutically acceptable salt thereof.

4. The compound according to claim 1 comprising 6-[(3,5-dimethylphenyl)selenenyl]-1-(ethoxymethyl)-5-isopropyluracil or a pharmaceutically acceptable salt thereof.

5. The compound according to claim 1 comprising 1-[(benzyloxy)methyl]-6-[(3,5-dimethylphenyl)selenenyl]-5-isopropyluracil or a pharmaceutically acceptable salt thereof.

6. An antiviral agent comprising as an active ingredient the compound of any one of claims 1–5 or a pharmaceutically acceptable salt thereof.

7. A pharmaceutical composition comprising the compound of any one of claims 1–6 or a pharmaceutically acceptable salt thereof in association with a pharmaceutical vehicle.

8. An intermediate represented by the following formula (IV) for preparing a compound represented by the following formula (I-a);

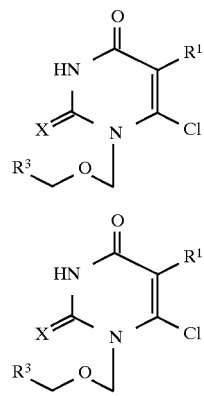

wherein $R^1$ represents ethyl or isopropyl, $R^2$ represents (3,5-dimethylphenyl)selenenyl, $R^3$ represents methyl or phenyl, and X represents oxygen.

9. A process for the production of a pyrimidine acyclonucleoside derivative represented by the following formula (I-a) comprising the steps of reacting a uracil represented by formula (II) with N,O-bis(trimethylsilyl)acetamide followed by tetrabutylammonium iodide and a chloromethyl ether represented by the following formula (III) and reacting a compound represented by the following formula (IV) with an aryl selenol in the presence of base

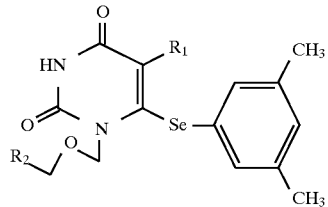

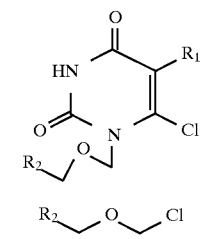

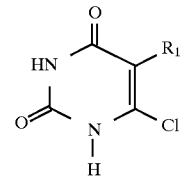

wherein $R_1$ represents ethyl or isoproply and $R_2$ represents methyl or phenyl.

* * * * *